(12) United States Patent
Hillis et al.

(10) Patent No.: US 8,499,764 B2
(45) Date of Patent: Aug. 6, 2013

(54) PORTABLE APPARATUS FOR ESTABLISHING AN ISOLATION FIELD

(75) Inventors: W. Daniel Hillis, Encino, CA (US); Elizabeth A. Sweeney, Seattle, WA (US); Clarence T. Tegreene, Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 343 days.

(21) Appl. No.: 12/802,025

(22) Filed: May 26, 2010

(65) Prior Publication Data
US 2011/0290257 A1    Dec. 1, 2011

(51) Int. Cl.
*A61F 13/00*    (2006.01)
*A61G 11/00*    (2006.01)
*A61N 1/30*    (2006.01)

(52) U.S. Cl.
USPC .............................. 128/847; 600/22; 604/19

(58) Field of Classification Search
USPC ... 600/22, 29–31; 604/19, 289–290; 128/847, 128/846
See application file for complete search history.

(56) References Cited

U.S. PATENT DOCUMENTS

| 2,473,033 | A | | 6/1949 | Letac |
| 3,252,400 | A | | 5/1966 | Madl, Jr. |
| 3,464,388 | A | * | 9/1969 | Stout ............................. 119/418 |
| 3,692,024 | A | | 9/1972 | Von Otto |
| 4,236,513 | A | * | 12/1980 | LoPiano ....................... 604/293 |
| 4,275,719 | A | | 6/1981 | Mayer |
| 4,367,728 | A | | 1/1983 | Mutke |
| 4,412,849 | A | | 11/1983 | Shahani |
| 4,432,354 | A | * | 2/1984 | Lasley ............................ 601/43 |
| 4,485,490 | A | | 12/1984 | Akers et al. |
| 4,550,713 | A | | 11/1985 | Hyman |
| 4,783,008 | A | | 11/1988 | Ikeuchi et al. |

(Continued)

FOREIGN PATENT DOCUMENTS

| EP | 1 008 334 A2 | 6/2000 |
| WO | WO 01/76501 A1 | 10/2001 |

OTHER PUBLICATIONS

3M Health Care; "3M™ Steri-Drape™ Cardiovascular Sheets with Ioban™ 2 Incise Film"; Bearing a date of 1998; pp. 1-4; located at http://mullimedia.3m.com/mws/mediawebserver?mwsId= 66666UuZjcFSLXTtlXf21XTEEVuQEcuZgVs6EVs6E666666--.

(Continued)

*Primary Examiner* — Patricia Bianco
*Assistant Examiner* — Tarla Patel
(74) *Attorney, Agent, or Firm* — Dorsey & Whitney LLP

(57) ABSTRACT

Apparatus and methods of their use are described herein. In an aspect, an apparatus includes: a structure defining an aperture at an engagement surface configured to reversibly seal to a surface on an individual body, and further defining an isolation field; at least one gas port; one or more gas inlets operably attached to the at least one gas port, the one or more gas inlets oriented to maintain a non-turbulent gas flow traversing at least a part of the surface on the individual body; one or more gas outlets distally positioned on the structure from the one or more gas inlets, the one or more outlets configured to release a gas from the isolation field while maintaining a positive pressure in the isolation field relative to the outside environment of the structure; and at least one sealable access site.

53 Claims, 10 Drawing Sheets

U.S. PATENT DOCUMENTS

| | | | |
|---|---|---|---|
| 4,850,534 A | 7/1989 | Takahashi et al. | |
| 4,860,643 A | 8/1989 | Spearow | |
| 4,941,618 A | 7/1990 | Hildebrand et al. | |
| 5,020,546 A | 6/1991 | Russo | |
| 5,060,644 A * | 10/1991 | Loori | 128/202.12 |
| 5,174,306 A | 12/1992 | Marshall | |
| 5,232,702 A | 8/1993 | Pfister et al. | |
| 5,312,385 A * | 5/1994 | Greco | 604/356 |
| 5,316,541 A | 5/1994 | Fischer | |
| 5,385,606 A | 1/1995 | Kowanko | |
| 5,480,410 A | 1/1996 | Cuschieri et al. | |
| 5,519,020 A | 5/1996 | Smith et al. | |
| 5,603,947 A | 2/1997 | Wong et al. | |
| 5,640,977 A | 6/1997 | Leahy et al. | |
| 5,661,132 A | 8/1997 | Eriksson et al. | |
| 5,832,925 A | 11/1998 | Rothrum | |
| 5,853,395 A | 12/1998 | Crook et al. | |
| 5,865,722 A * | 2/1999 | Heng | 600/21 |
| 5,905,092 A | 5/1999 | Osborne et al. | |
| 5,979,450 A | 11/1999 | Baker et al. | |
| 6,179,804 B1 | 1/2001 | Satterfield | |
| 6,199,551 B1 | 3/2001 | Kuslich | |
| 6,383,162 B1 | 5/2002 | Sugarbaker | |
| 6,494,858 B1 | 12/2002 | van der Linden | |
| 6,551,577 B1 | 4/2003 | Chen | |
| 6,592,451 B2 | 7/2003 | Tang | |
| 6,742,522 B1 | 6/2004 | Baker et al. | |
| 6,810,288 B2 | 10/2004 | Joshi | |
| 6,967,261 B1 | 11/2005 | Soerens et al. | |
| 6,987,133 B2 | 1/2006 | Chen | |
| 7,083,806 B2 | 8/2006 | Rippon et al. | |
| 7,504,385 B2 | 3/2009 | Binetti et al. | |
| 7,776,028 B2 * | 8/2010 | Miller et al. | 604/543 |
| 2004/0049165 A1 * | 3/2004 | Thompson et al. | 604/313 |
| 2004/0116770 A1 * | 6/2004 | O'Connor et al. | 600/21 |
| 2005/0148984 A1 | 7/2005 | Lindsay et al. | |
| 2005/0181170 A1 | 8/2005 | Fearing et al. | |
| 2005/0271869 A1 | 12/2005 | Jackson | |
| 2006/0185670 A1 * | 8/2006 | Loori et al. | 128/202.12 |
| 2006/0293630 A1 * | 12/2006 | Manna et al. | 604/327 |
| 2007/0208141 A1 | 9/2007 | Shull et al. | |
| 2008/0169059 A1 | 7/2008 | Messersmith et al. | |
| 2009/0131883 A1 | 5/2009 | Av-Gay et al. | |
| 2009/0143720 A1 * | 6/2009 | Hovorka | 604/23 |
| 2009/0163661 A1 | 6/2009 | Shull et al. | |
| 2009/0173341 A1 | 7/2009 | Reinhold et al. | |
| 2009/0240000 A1 | 9/2009 | Shull et al. | |
| 2009/0247704 A1 | 10/2009 | Shull et al. | |
| 2009/0298999 A1 | 12/2009 | Shull et al. | |
| 2009/0302545 A1 | 12/2009 | Haynes | |
| 2010/0035815 A1 | 2/2010 | Li et al. | |

OTHER PUBLICATIONS

3M Medical Division; "3M™ Steri-Drape™ Cardio/Chest Drape with Ioban™ 2 Incise Film—6682"; Bearing a date of 2007; pp. 1-2; located at http://multimedia.3m.com/mws/mediawebserver?mwsId=66666UuZjcFSLXTtnxTy5XFVEVuQEcuZgVs6EVs6E666666--.

Anderson, Paula J; "History of Aerosol Therapy: Liquid Nebulization to MDIs to DPIs"; Respiratory Care; Bearing a date of Sep. 2005; pp. 1139-1150; vol. 50, No. 9.

Brett, David; "A Review of Collagen and Collagen-based Wound Dressings"; Wounds; Bearing a date of 2008; pp. 1-5; vol. 20, No. 12; HMP Communications.

Brook, Itzhak, et al.; "Aerobic and Anaerobic Microbiology of Surgical-Site Infection Following Spinal Fusion"; Journal of Clinical Microbiology; Bearing a date of Mar. 1999; pp. 841-843; vol. 37, No. 3.

Dassault Systèmes Solidworks Corp.; "SolidWorks Premium 2010"; Bearing a date of 2009; pp. 1-4.

Elsner, Jonathan J., et al.; "Novel Biodegradable Composite Wound Dressings With Controlled Release of Antibiotics: Microstructure, Mechanical and Physical Properties"; Journal of Biomedical Materials Research B: Applied Biomaterials; Bearing a date of May 2010; pp. 425-435; vol. 93B, Issue 2; Wiley Periodicals, Inc.

Gago, Manuel, et al.; "A Comparison of Three Silver-containing Dressings in the Treatment of Infected, Chronic Wounds"; Wounds; Bearing a date of Oct. 2008; pp. 273-278; vol. 20, No. 10.

Germfree; "Historical Usage of Laminar Airflow"; Downloaded on Jul. 17, 2007; pp. 1-3; located at http://www.germfree.com/.

Khongtong, Sureurg, et al.; "A Smart Adhesive Joint: Entropic Control of Adhesion at a Polymer/Metal Interface"; Journal of the American Chemical Society; Bearing a date of 2002; pp. 7254-7255; vol. 124, No. 25; American Chemical Society.

Kitamura, Masahiro, et al.; "Periodontal Tissue Regeneration Using Fibroblast Growth Factor -2: Randomized Controlled Phase II Clinical Trial"; PLoS ONE; Bearing a date of Jul. 2008; pp. 1-11; vol. 3, Issue 7, e2611.

Kowalski, W.J., et al.; "MERV Filter Models for Aerobiological Applications"; AIR Media; Bearing a date of Summer 2002; pp. 13-17 (pp. 1-12).

Li, Yali, et al.; "Shell crosslinked nanoparticles carrying silver antimicrobials as therapeutics"; Chemical Communications; Bearing a date of 2010; pp. 121-123; vol. 46; The Royal Society of Chemistry.

Mangram, Alicia J., et al.; "Guideline for Prevention of Surgical Site Infection, 1999"; Infection Control and Hospital Epidemiology; Bearing a date of Apr. 1999; pp. 247-278; vol. 20, No. 4.

Masliyah, Jacob H.; "On laminar flow in curved semicircular ducts"; Journal of Fluid Mechanics; Bearing a date of 1980; pp. 469-479 plus 2 pages; vol. 99, Part 3; Cambridge University Press.

Matsumoto, LT COL Teruo, et al.; "Antibiotic Topical Spray Applied in a Simulated Combat Wound"; Archives of Surgery; Bearing a date of Aug. 1967; pp. 288-294; vol. 95.

Medscape; "Determinants of Infection"; Medscape from WebMD; Bearing dates of 2003 and Apr. 28, 2004; pp. 1-3.

Mendes, Paula M; "Stimuli-responsive surfaces for bio-applications"; Chemical Society Reviews; Bearing a date of Nov. 2008; pp. 2512-2529; vol. 37, No. 11; The Royal Society of Chemistry.

Meykadeh, Nuschin, et al.; "Topical application of plasmid DNA to mouse and human skin"; Journal of Molecular Medicine; Bearing a date of 2005; pp. 897-903; vol. 83; Springer-Verlag.

Nichols, Ronald Lee; "Preventing Surgical Site Infections: A Surgeon's Perspective"; Emerging Infectious Diseases; Bearing a date of Mar.-Apr. 2001; pp. 220-224; vol. 7, No. 2.

Ogata, Norio, et al.; "Protective effect of low-concentration chlorine dioxide gas against influenza A virus infection"; Journal of General Virology; Bearing a date of 2008; pp. 60-67; vol. 89; SGM.

Pall Corporation; "Acro® 50 Vent Devices with Emflon® II Membrane"; Bearing a date of May 21, 2010; pp. 1-2; located at http://www.pall.com/variants/pdf/pdf/laboratory_19977.pdf Pall Corporation; "Emflon® PFA Filter Cartridges"; Bearing a date of May 23, 2010; pp. 1-3; located at http://www.pall.com/variants/pdf/pdf/foodandBev_47990.pdf.

Pall Corporation; "HDC® II Filter Cartridges for Gas Applications"; Bearing a date of May 23, 2010; pp. 1-3; located at http://www.pall.com/variants/pdf/pdf/biophram_28614.pdf.

Passage, Jurgen, et al.; "BioGlue: A Review of the Use of This New Surgical Adhesive in Thoracic Surgery"; ANZ Journal of Surgery; Bearing a date of 2005; pp. 315-318; vol. 75.

Roelants, P., et al.; "Evaluation of a Commercial Air Filter for Removal of Viruses from the Air"; Applied Microbiology; Bearing a date of Oct. 1968; pp. 1465-1467; vol. 16, No. 10; American Society for Microbiology.

Silver, Simon, et al.; "Silver as biocides in burn and wound dressings and bacterial resistance to silver compounds"; Journal of Industrial Microbiology and Biotechnology; Bearing a date of 2006; pp. 627-634; vol. 33.

Singhal, Hemant, et al.; "Wound Infection: eMedicine General Surgery"; eMedicine from WebMD; Bearing a date of Sep. 8, 2009; Printed on Oct. 13, 2009; pp. 1-26; located at http://emedicine.medscape.com/article/188988-print.

Smith, Sydney; "Good Unintended Consequences"; Tech Central Station; Bearing a date of Apr. 4, 2003; pp. 1-4.

Smooth-On; "Skin Tite Platinum Silicone Bio-Adhesive & Appliance Builder"; Bearing a date of Sep. 2, 2008; pp. 1-2; located at http://www.smooth-on.com/tb/files/Skin_Tite.pdf.

Spraying Systems Co.; "FloMax® Air Atomizing Nozzles: High Efficiency Nozzles Offer Tight Control of Drop Size and Spray Coverage, Provide Precise Performance"; Bearing a date of 2005; pp. 1-8; located at http://service.spray.com/web/register/view_lit.asp?code=B487C.

Thanik, VD, et al.; "Topical matrix-based siRNA silences local gene expression in a murine wound model"; Gene Therapy; Bearing a date of 2007; pp. 1305-1308; vol. 14; Nature Publishing Group.

Thomas, Xavier; "Silicone Adhesives in Healthcare Applications"; Dow Corning Healthcare Industry; Bearing a date of 2003; pp. 1-6.

Vogel, Michael J., et al.; "Capillarity-based switchable adhesion"; PNAS; Bearing a date of Feb. 23, 2010; pp. 3377-3381; vol. 107, No. 8.

Walton, M. A., et al.; "The Efficacy of Polysporin First Aid Antibiotic Spray* (Polymyxin B Sulfate and Bacitracin Zinc) Against Clinical Burn Wound Isolates"; Journal of Burn Care & Rehabilitation; Bearing a date of Mar./Apr. 1991; pp. 116-119; vol. 12, No. 2.

Whitt, Suzy; "Air Filtration and the Use of HEPA Filters in Biological Safety Cabinets"; Nuaire; Printed on Mar. 19, 2010; pp. 1-7; located at http://www.nuaire.com/download/whitepaper/use_of_hepa_filters.pdf.

Yacoby, Iftach, et al.; "Antibacterial nanomedicine"; Nanomedicine; Bearing a date of 2008; pp. 329-341; vol. 3, No. 3; Future Medicine Ltd.

U.S. Appl. No. 13/924,048, Hillis et al.

* cited by examiner

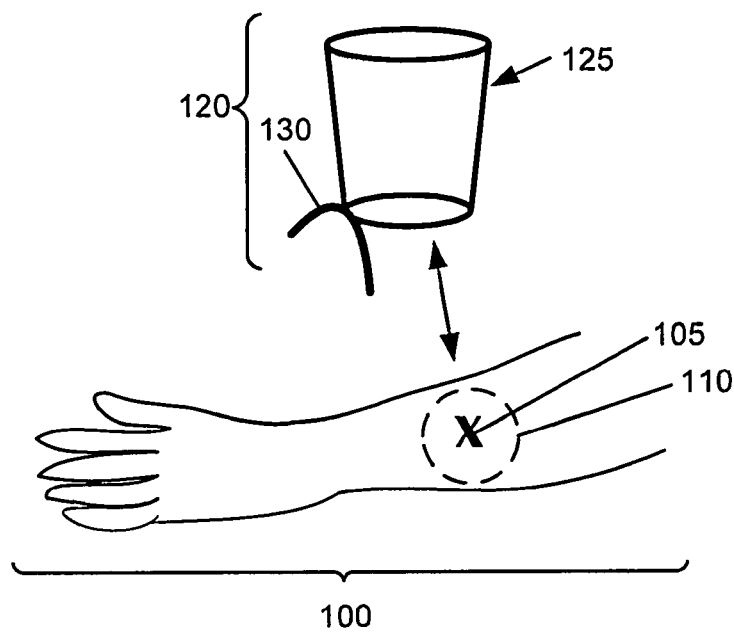
FIG. 1A
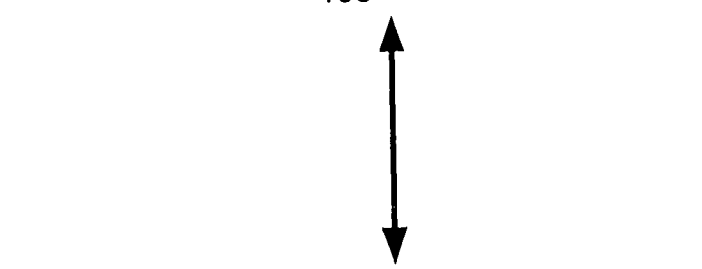
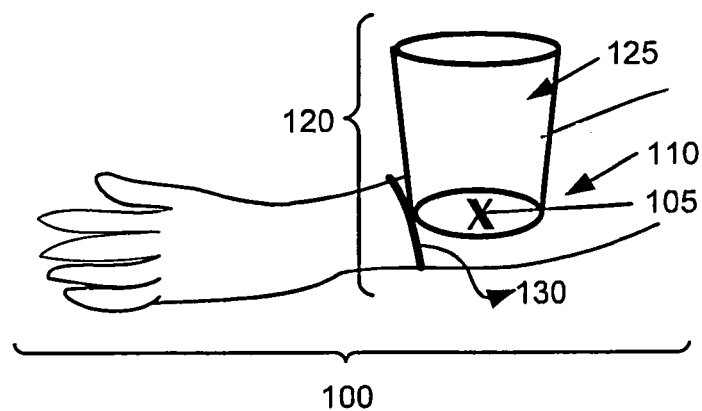
FIG. 1B

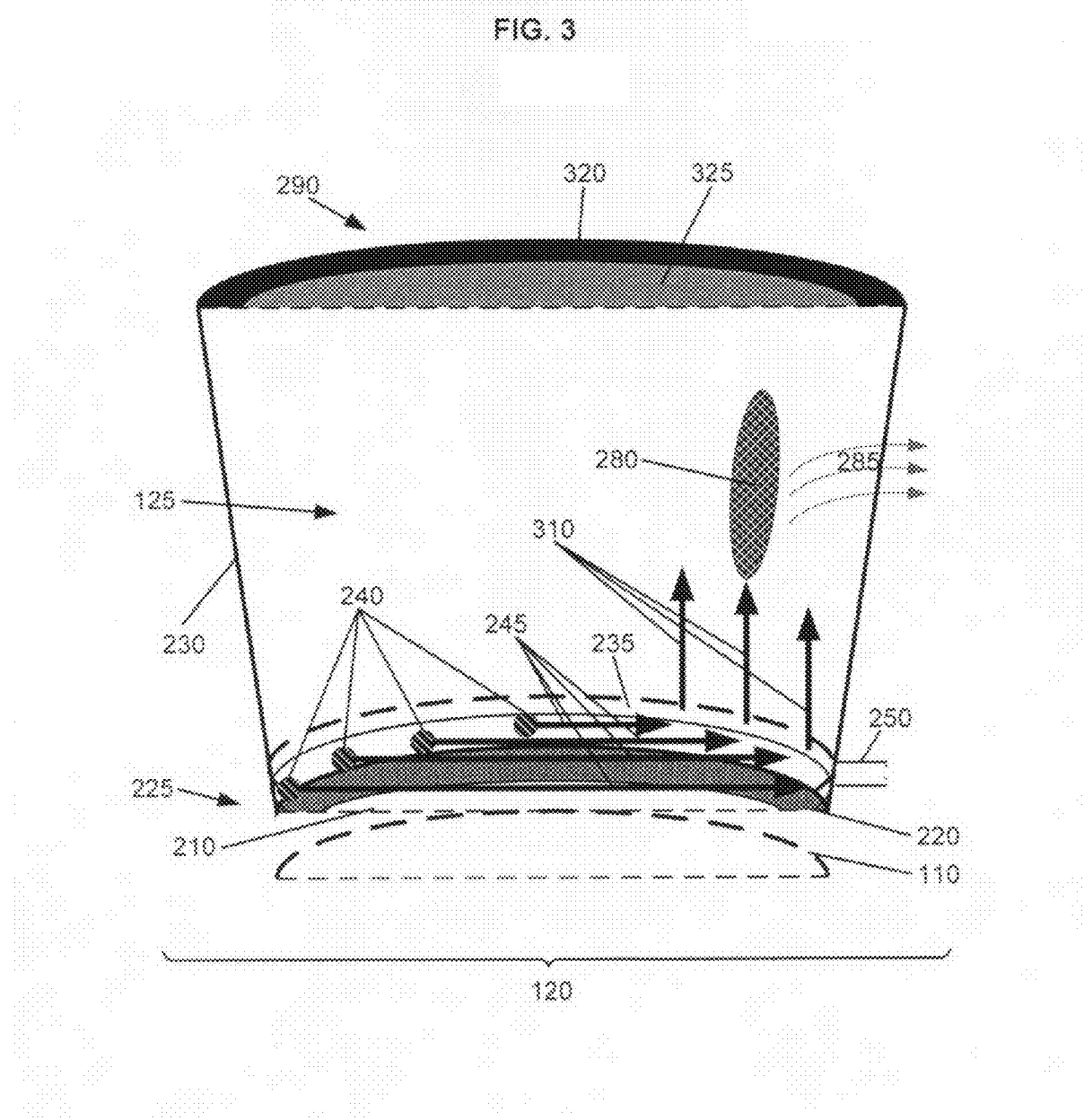

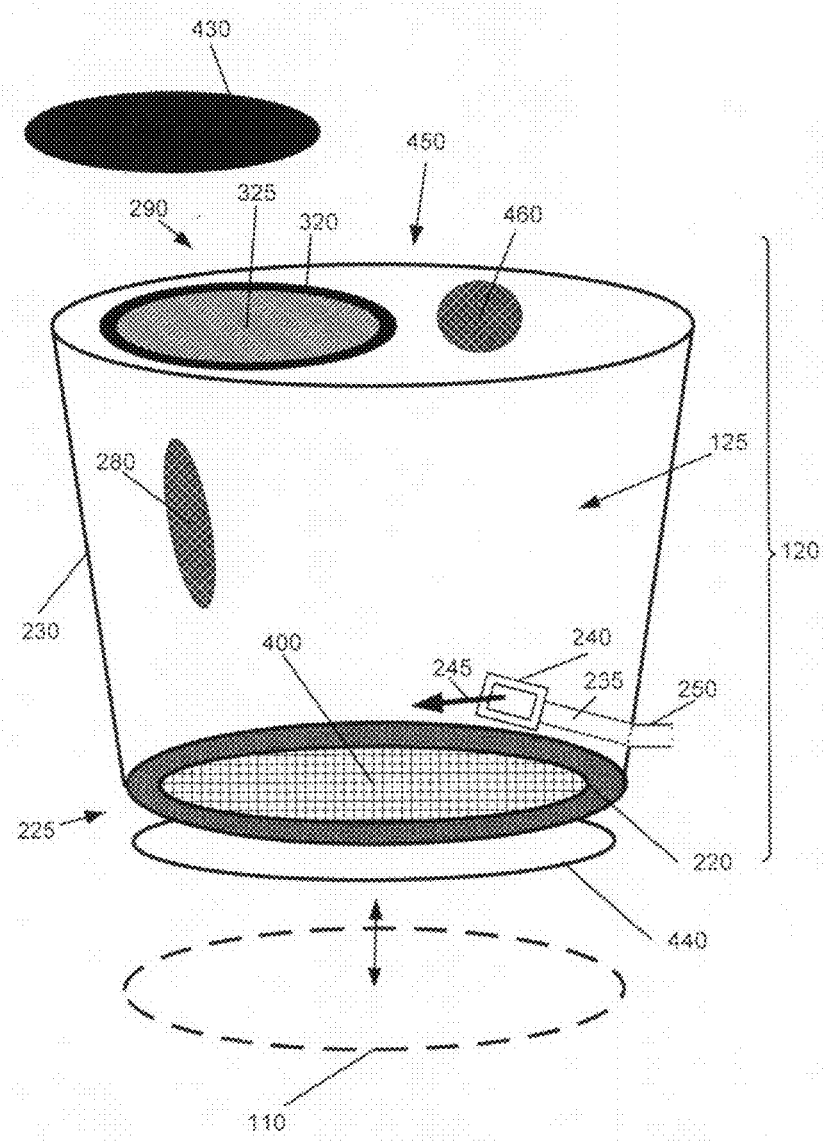

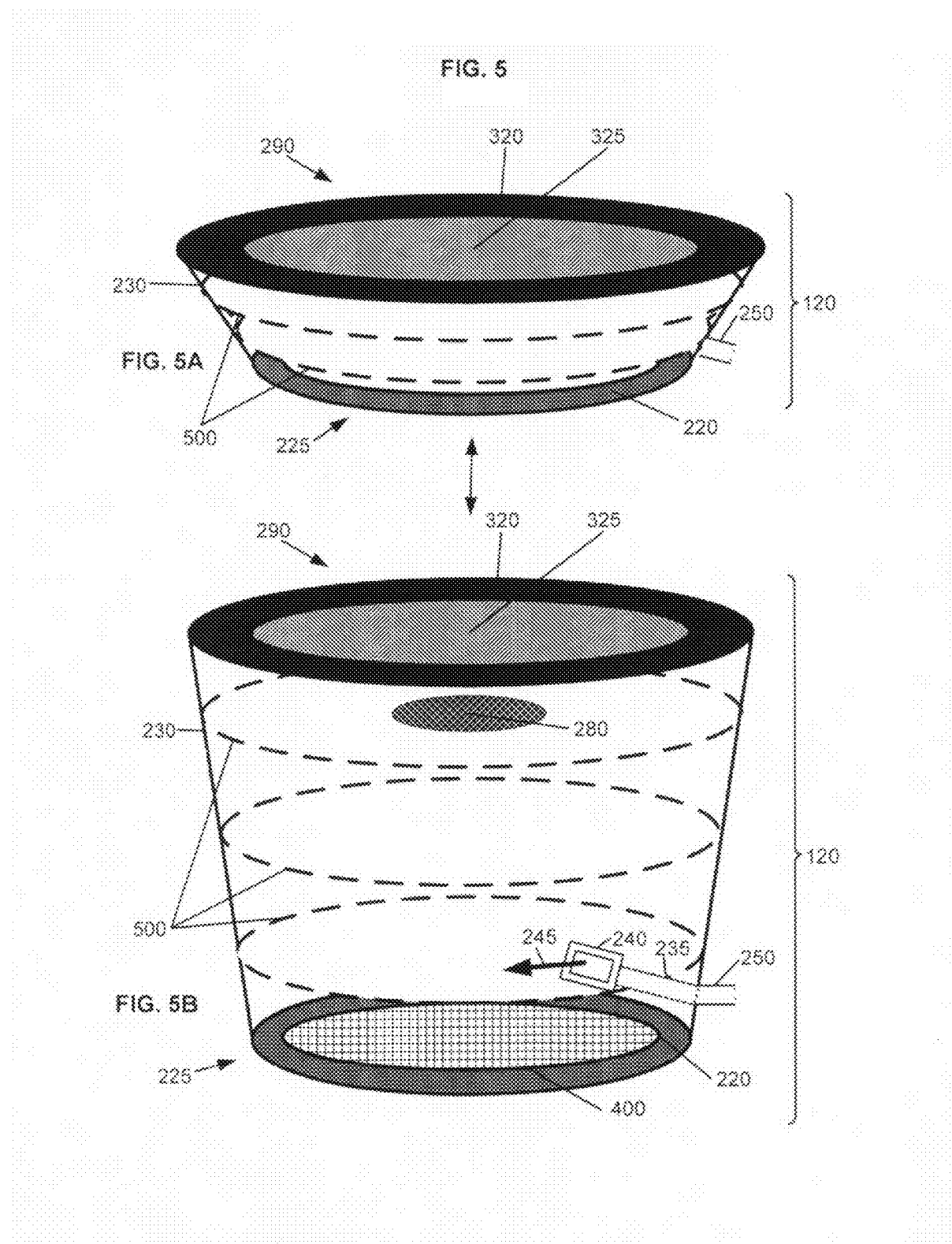

PORTABLE APPARATUS FOR ESTABLISHING AN ISOLATION FIELD

SUMMARY

In an aspect, a system includes but is not limited to an apparatus, including: a structure defining an aperture at an engagement surface configured to reversibly seal to a surface on an individual body, and further defining an isolation field; at least one gas port; one or more gas inlets operably attached to the gas port, the one or more gas inlets oriented to maintain a non-turbulent gas flow traversing at least a part of the surface of the individual body; one or more gas outlets distally positioned on the structure from the one or more gas inlets, the one or more gas outlets configured to release a gas from the isolation field while maintaining positive pressure in the isolation field relative to an outside environment of the structure; and at least one sealable access site. In an aspect, a system includes but is not limited to an apparatus, including: a structure configured to define an isolation field, wherein the structure includes an engagement surface configured to sealably couple to a surface on an individual body, and further defining a region of the individual body that includes a medical site; a plurality of gas inlets oriented to maintain non-turbulent flow of a gas in parallel with at least a part of the surface on the individual body; at least one gas port, the at least one gas port configured for supplying the gas to the plurality of gas inlets; one or more gas outlets positioned on the structure distal to the plurality of gas inlets, the one or more gas outlets configured to release the gas from the structure while maintaining positive pressure in the structure relative to the outside environment of the structure; at least one sealable access site between the isolation field and the exterior of the structure; and at least one gas source. In an aspect, an apparatus includes: a structure configured to define an isolation field, wherein the structure includes an engagement surface configured to sealably couple to a surface on an individual body, and further defining a region of the individual body that includes a medical site; a film within the engagement surface, wherein the film is oriented in parallel with at least a part of the surface on the individual body; a plurality of gas inlets configured to maintain non-turbulent flow of a gas oriented in parallel with at least a part of the surface on the individual body; at least one gas port, the at least one gas port configured for supplying the gas to the plurality of gas inlets; one or more gas outlets positioned on the structure distal to the plurality of gas inlets, the one or more gas outlets configured to release the gas from the structure while maintaining positive pressure in the structure relative to the outside environment of the structure; at least one sealable access site between the isolation field and the exterior of the structure; and at least one gas source. In addition to the foregoing, other system aspects are described in the claims, drawings, and text forming a part of the present disclosure.

In an aspect, a method for establishing an isolation field around a medical site includes but is not limited to: sealably coupling an apparatus over a medical site to define an isolation field; maintaining a non-turbulent flow of gas within the apparatus; and outletting gas from the apparatus through one or more gas outlets while maintaining positive pressure within the isolation field. In addition to the foregoing, other method aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1A is a schematic of an apparatus.
FIG. 1B is a schematic of the apparatus depicted in FIG. 1A.
FIG. 3 is a cross-sectional view of an apparatus.
FIG. 4 is a schematic of an apparatus.
FIG. 5A is a schematic of an apparatus in a compressed form.
FIG. 5B is a schematic of the apparatus of FIG. 5A in a decompressed form.

DETAILED DESCRIPTION

Figure 2A:
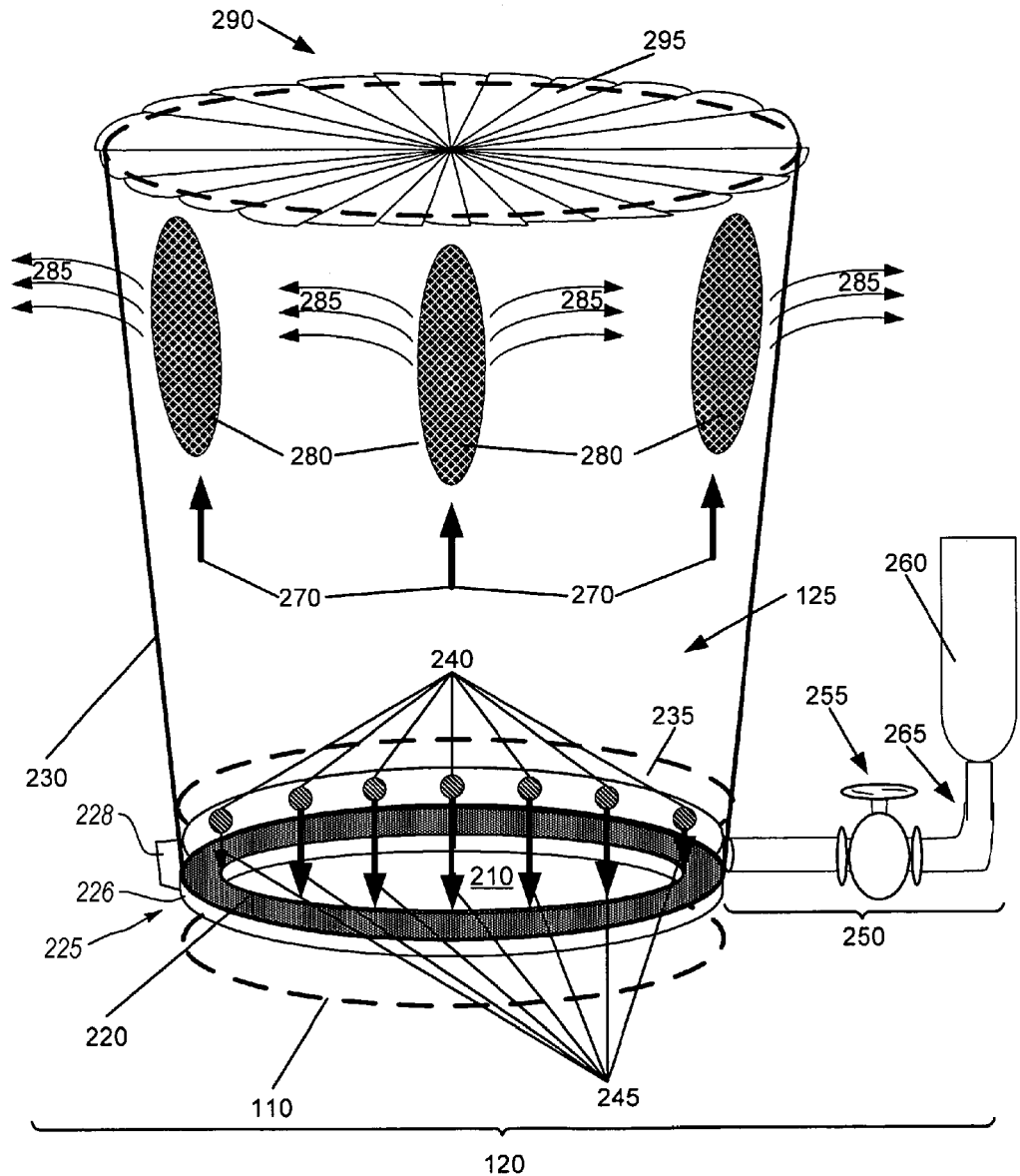
FIG. 2 is a schematic of an apparatus.

In some embodiments, an apparatus includes: a structure defining an aperture at an engagement surface on an individual body, and further defining an isolation field; at least one gas port; one or more gas inlets operably attached to the gas port, the one or more gas inlets oriented to maintain a non-turbulent gas flow traversing at least a part of the surface on the individual body; one or more gas outlets distally positioned on the structure from the one or more gas inlet, the one or more outlets configured to release a gas from the isolation field while maintaining positive pressure in the isolation field relative to the outside environment of the structure; and at least one sealable access site.

In some embodiments, an apparatus includes: a structure configured to define an isolation field, wherein the structure includes an engagement surface configured to sealably couple to a surface on an individual body, and further defining a region of the individual body that includes a medical site; a plurality of gas inlets oriented to maintain non-turbulent flow of a gas in parallel with at least a part of the surface on the individual body; at least one gas port, the at least one gas port configured for supplying the gas to the plurality of gas inlets; one or more gas outlets positioned on the structure distal to the plurality of gas inlets, the one or more gas outlets configured to release the gas from the structure relative to the outside environment of the structure; at least one sealable access site between the isolation field and the exterior of the structure; and at least one gas source.

In some embodiments, an apparatus includes a structure configured to define an isolation field, wherein the structure includes: an engagement surface configured to sealably couple to a surface on an individual body, and further defining a region of the individual body that includes a medical site; a film within the engagement surface, wherein the film is oriented in parallel with at least a part of the surface on the individual body; a plurality of gas inlets configured to maintain non-turbulent flow of a gas oriented in parallel with at least a part of the surface on the individual body; at least one gas port, the at least one gas port configured for supplying the gas to the plurality of gas inlets; one or more gas outlets positioned on the structure distal to the plurality of gas inlets, the one or more gas outlets configured to release the gas from the structure while maintaining positive pressure in the structure relative to the outside environment of the structure; at least one sealable access site between the isolation field and the exterior of the structure; and at least one gas source.

Methods described herein include a method for establishing an isolation field around a medical site, including: sealably coupling an apparatus over a medical site to define an isolation field; maintaining a non-turbulent flow of gas within the apparatus; and outletting gas from the apparatus through one or more gas outlets while maintaining positive pressure within the isolation field.

In the detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Apparatus and methods such as those described herein define an isolation field over a region on an individual body. Apparatus and methods such as those described herein define an isolation field adjacent to an individual body. The region of the individual body may include a medical site.

FIGS. 1A and 1B depict aspects of the methods and apparatus described herein. The use of the same symbols in different drawings typically indicates similar or identical items. A portion of an individual body, such as a hand and arm 100, may include a medical site 105. Although a hand and an arm are depicted in FIGS. 1A and 1B, in various embodiments the apparatus and methods may be configured for use with other parts of the human body. For example, the apparatus may be manufactured of a size and shape suitable for use relative to a human abdominal region, and embodiments of the methods may be utilized in relation to the human abdominal region. For example, the apparatus may be manufactured of a size and shape suitable for use on a human leg, ankle or foot, and embodiments of the methods may be utilized in relation to the human leg, ankle, or foot. For example, the apparatus may be manufactured of a size and shape suitable for use with a human torso, and embodiments of the methods may be utilized in relation to the human torso. For example, the apparatus may be manufactured of a size and shape suitable for use relative to a hip region, and embodiments of the methods may be utilized in relation to the hip region. For example, the apparatus may be manufactured of a size and shape suitable for use on a human shoulder, and embodiments of the methods may be utilized in relation to the human shoulder. For example, the apparatus may be manufactured of a size and shape suitable for use relative to a human head and neck, and embodiments of the methods may be utilized in relation to the human head and neck.

Although a human hand and arm 100 are depicted in FIGS. 1A and 1B, in some embodiments the apparatus and methods described herein may be suitable for veterinary applications. For example, the apparatus and methods described herein may be applicable for use with animals such as cats, dogs, or horses. For example, a dog may receive an injury while hiking with a person, and apparatus and methods such as those described herein may be utilized to stabilize the injury before the animal is taken to a veterinary clinic. For example, a horse may receive a cut in an accident, and apparatus and methods such as those described herein may be utilized to stabilize the injury before a veterinarian is available to evaluate the animal. For example, apparatus and methods such as those described herein are envisioned as applicable to service animals, such as dogs or horses. For example, a service animal may receive an injury while in a remote location supporting human activity, and apparatus and methods such as those described herein may be of use to stabilize the injury before veterinary assistance is available.

A region of the body 110 which may surround a medical site 105 and include a medical site 105 is depicted in FIG. 1A prior to covering by the apparatus 120. A region of the body 110 which may surround a medical site 105 and include a medical site 105 is depicted in FIG. 1B after the region 110 is covered by the apparatus 120. As illustrated in FIGS. 1A and 1B, during operation of the apparatus 120, a region of the body 110 which may include a medical site 105 is isolated within the isolation field 125 within the apparatus 120. The apparatus 120 includes an isolation field 125 internal to the structure of the apparatus 120 when the apparatus 120 is reversibly attached to the region of the body 110. As depicted in FIG. 1B, an isolation field 125 is created when the apparatus 120 is positioned adjacent to the region of the body 110. The isolation field 125 is maintained while the apparatus 120 is positioned relative to the region of the body 110. An engagement surface of the apparatus 120 is configured to reversibly seal to at least part of the region of the body 110, wherein the apparatus 120 may surround a medical site 105 and include a medical site 105 within an isolation field 125 within the apparatus 120. The engagement surface of the apparatus 120 is positioned on a surface of the apparatus 120 configured for attachment to the region of the body 110.

The isolation field 125 within an apparatus 120 may be configured to substantially sequester the region of the body 110 including a medical site 105 within the isolation field 125. The isolation field 125 within an apparatus 120 may be configured to substantially inhibit movement of particulate matter between the interior of the isolation field 125 and the region external to the apparatus 120. For example, the isolation field 125 within an apparatus 120 may be configured to substantially inhibit movement of microbes between the interior of the isolation field 125 and the region external to the apparatus 120. For example, the isolation field 125 within an apparatus 120 may be configured to substantially inhibit movement of viral particles between the interior of the isolation field 125 and the region external to the apparatus 120. For example, the isolation field 125 within an apparatus 120 may be configured to substantially inhibit movement of bacteria between the interior of the isolation field 125 and the region external to the apparatus 120. For example, the isolation field 125 within an apparatus 120 may be configured to substantially inhibit movement of fungal particles between the interior of the isolation field 125 and the region external to the apparatus 120. For example, the isolation field 125 within an apparatus 120 may be configured to substantially inhibit movement of wound debris between the interior of the isolation field 125 and the region external to the apparatus 120.

A region of the body 110 including a medical site 105 may be isolated within the isolation field 125 within the apparatus 120 for the purpose of preventing future infection. For example, the isolation field 125 within an apparatus 120 may be configured to substantially inhibit movement of microbes between the interior of the isolation field 125 and the region external to the apparatus 120. A region of the body 110 including a medical site 105 may be isolated within the isolation field 125 within the apparatus 120 for the purpose of inhibiting spread of a pathogenic agent. For example, the pathogenic agent may be subject to conditions that inhibit the growth, replication, persistence and/or relocation of the pathogenic agent within the isolation field 125. For example, the pathogenic agent may be subject to temperature conditions, humidity, or chemical compositions that inhibit the growth, replication, persistence, durability and/or relocation of the pathogenic agent within the isolation field 125. A region of the body 110 including a medical site 105 may be isolated within the isolation field 125 within the apparatus 120 for the purpose of promoting healing. For example, the isolation field 125 within an apparatus 120 may be configured to promote healing conditions at the medical site 105. For example, the apparatus 120 may be configured to release healing-promoting compounds within the isolation field 125 at the medical site 105. For example, the apparatus 120 may include healing-promoting compounds at the surface of the apparatus within the isolation field 125 at the medical site 105. A region of the body 110 may be isolated within the isolation field 125 within the apparatus 120 for the purpose of inhibiting spread of a hazardous agent including, for example, a biological or chemical agent such as a weaponized biological or chemical agent. A region of the body 110 may be isolated within the isolation field 125 within the apparatus 120 for the purpose of inhibiting spread of a hazardous agent including, for example, a therapeutic agent (e.g. radioactive element, or a chemotherapeutic anti-cancer agent that may be, for example, a teratogen). For example, the isolation field 125 within an apparatus 120 may be configured to restrict relative movement of a hazardous agent between the medical site 105 and the region external to the apparatus 120.

Although a medical site 105 is depicted as an "X" symbol in FIGS. 1A and 1B for the purposes of visualization, a medical site 105 may include a variety of conditions. A medical site 105 may include a lesion, such as a wound, papule, neoplasia, rash, or contaminated region of an individual body. For example, a medical site 105 may include an externally visible wound, such as a laceration, cut, puncture wound, heat burn, chemical burn, or other injury site. A medical site 105 may include imbedded contaminating material, such as material involved in creating a wound, or contaminating material that was located on the skin surface prior to wound creation, or contaminating material that entered the region after or simultaneously with wound creation. For example, a medical site 105 may include debris, including wood, metal, cloth or plastic. For example, a medical site 105 may include shrapnel, shot, shells or fragments and/or casings thereof. For example, a medical site 105 may include chemical agents, such as petroleum products or industrial chemicals. For example, a medical site 105 may include pathogenic material, such as debris contaminated with at least one pathogen. For example, a medical site 105 may include allergenic material, such as debris contaminated with at least one allergen. The allergen may be an actual or potential allergen, for example an allergenic agent to which only a portion of a population is sensitive. For example, a medical site 105 may be isolated for the purpose of inhibiting contamination by a contagion, a pathogen, an allergen contaminant, or a chemical agent. A medical site 105 may include a region of future medical intervention, such as the skin region over an internal infection site. A medical site 105 may include a region of potential medical intervention, such as the skin region over an internal infection site. The skin region over an internal infection site, for example, may be isolated within the isolation field 125 within the apparatus 120 in order to support medical intervention to treat an infection. The skin region over an internal infection site may be isolated within the apparatus 120 in order to sequester a medical site 105 that may be likely to rupture the external skin surface. A medical site 105 may include a region subject to the process of tattooing. A region of the body 110 including a medical site 105 may include a region of future medical intervention such as the skin region over a site chosen for surgical intervention. A medical site 105 may include a region chosen for incision. A medical site 105 may include a region chosen for biopsy. A medical site 105 may include a region chosen for access to an internal tissue. A medical site 105 may include a region chosen for laparoscopic access, including insufflation. A medical site 105 may include a region chose for arthroscopic intervention. A medical site 105 may include a wound.

Wounds are classified into four categories based on the risk of bacterial contamination: Class I, Clean (e.g. aseptic surgical wound); Class II, Clean-contaminated (e.g. a surgical wound entering a viscus); Class III, Contaminated (e.g. an open traumatic wound with foreign material); and Class IV, Dirty (e.g. an open traumatic wound with necrotic tissues, bacteria, and/or significant amounts of foreign materials). Even in the relatively aseptic environment of an operating theater, contamination of a Class I or II surgical wound by bacteria from a provider or the patient remains a major cause of morbidity in postoperative patients. See, for example, Brook and Frazier, "Aerobic and Anaerobic Microbiology of Surgical-Site Infection Following Spinal Fusion," *Journal of Clinical Microbiology*, Vol. 37, No. 3 (1999), which is herein incorporated by reference. See, for example, International Patent Application No. WO01/76501 A1, to Jennings et al., titled "Surgical Implant System," which is herein incorporated by reference. Surgical site infections are a common nosocomial infection, causing increases in hospitalization stay and costs. See, for example, Mangram et al., "Guideline for Prevention of Surgical Site Infection, 1999," *Infection Control and Hospital Epidemiology*, Vol. 20, No. 4, pages 247-278, which is herein incorporated by reference. See, for example, Nichols "Preventing Surgical Site Infections: a Surgeon's Perspective," *Emerging Infectious Diseases*, Vol. 7, No. 2, (2001), which is herein incorporated by reference. See, for example, Singhal and Kaur, "Wound Infection," *eMedicine*, updated on Sep. 8, 2009, which is herein incorporated by reference. See, for example, U.S. Pat. No. 6,383,162 to Sugarbaker, titled "Apparatus and Method for Abdomino-Pelvic Chemotherapy Perfusion and Lavage," which is herein incorporated by reference. See, for example, "Determinants of Infection," MedScape, dated Apr. 28, 2004, Copyright 2003, which is herein incorporated by reference. Such a risk becomes even greater in circumstances of accident or combat, in the absence of a sterile environment, whether dealing with an open wound needing repair or a fresh surgical incision. Apparatus and methods described herein are envisioned as being of use in such situations.

Even within relatively protected environments, traditional preventative measures, such as prophylactic antibiotics, are becoming less available. Overuse has led to antibody-resistant microbes, especially in hospital settings, so physicians are becoming reluctant to prescribe antibiotics prophylactically, especially newer, last defense drugs. The apparatus and methods described herein may be useful to minimize potential contamination and, therefore, the need for prophylactic antibiotics. Additionally, an increasing number of surgeries involve minimally invasive techniques such as laparoscopic, arthroscopic, or microscopic techniques. These techniques minimize the size of the surgical wound, but require maintenance of smaller surgical fields. See, for example, U.S. Pat. No. 5,853,395 to Crook et al., titled "Extracorporeal Pneumoperitoneum Enclosure and Method of Use," which is herein incorporated by reference. See, for example, U.S. Pat. No. 2,473,033 to Letac, titled "Sterilized and Air-Conditioned Chamber for Surgical Uses," which is herein incorporated by reference. The apparatus and methods described herein may be of use with minimally invasive surgical techniques. Moreover, the increasing costs of medical care and the concern of blood-borne pathogens have directed emphasis toward low cost, disposable equipment. The apparatus and methods described herein may be fabricated in a single-use, disposable format suitable for such situations. Surfaces of the apparatus 120, including internal surfaces, may be substantially sterile prior to use.

Modern techniques and equipment are also allowing more on-site treatment of accident or combat patients. See, for example, U.S. Pat. No. 4,485,490 to Akers, titled "Apparatus for Treating Casualties in a Contaminated Area," which is herein incorporated by reference. See, for example, U.S. Pat. No. 4,367,728 to Mutke, titled "Isolation Apparatus," which is herein incorporated by reference. See, for example, "Good Unintended Consequences," Smith, Tech Central Station, dated Apr. 4, 2003, which is herein incorporated by reference. On-site treatment can provide a better chance of survival, but also raises issues regarding the provision of a sterile environment. Additionally, treatment, for example emergency treatment, may be provided to patients who are possibly carrying infectious pathogens. For example, first responders, good Samaritans, surgeons, and other care providers may be exposed to the human immunodeficiency virus (HIV), a hepatitis virus, or other blood-borne pathogens while providing assistance to a wounded individual. The apparatus described herein may be fabricated in sizes and weights for easy portability and use in emergency, accident and combat-related injuries. Similarly, the apparatus described herein may be fabricated in sizes and weights for storage in medical safety cabinets in high risk environments, such as workplaces where hazardous chemicals are present or in workplaces where accidental burns or wounds are of concern.

An isolation field 125 is formed within the structure of the apparatus 120 and adjacent to the medical site 105. The isolation field 125 generally defines an area including a region of the surface of the body and the space adjacent to the region of the body. The isolation field 125 is substantially isolated from egress of material from the isolation field 125. For example, the isolation field 125 may include contaminants, such as contaminants present on the medical site 105 prior to placement of the apparatus over the medical site 105. For example, the isolation field 125 may include a biohazardous material, such as a material present on the medical site 105 prior to placement of the apparatus over the medical site 105. For example, the isolation field 125 may include debris, such as debris present at the medical site 105 prior to placement of the apparatus over the medical site 105. The isolation of a medical site 105 within an isolation field 125 substantially separates the medical site 105 from material movement between the medical site 105 and the region exterior to the isolation field 125. The isolation field 125 is substantially isolated from entry of material into the isolation field 125. For example, the isolation field 125 may be substantially sterile, with minimal contamination from outside of the isolation field 125. For example, an isolation field 125 substantially contains contaminants from a medical site 105, such as bloodborne pathogens, chemical contaminants, or debris within the isolation field 125. For example, an apparatus 120 substantially blocks contaminants from the environment surrounding the isolation field 125, such as dirt, chemical contaminants, bacteria, or debris from entering the isolation field 125 and therefore from coming into contact with the medical site 105.

The apparatus 120 may include a restraining unit 130. A restraining unit 130 is configured to provide stability to the location and placement of the apparatus 120 at the region of the body 110. A restraining unit 130 is configured to stabilize the position of the engagement surface relative to a region of an individual body 110. A restraining unit 130 may include, for example, a strap configured to reversibly fasten around a portion of an individual body, as depicted in FIG. 1B. A restraining unit 130 may include, for example, an adhesive covering configured to reversibly attach to a portion of an individual body. A restraining unit 130 may include, for example, an elastic band of a size and shape suitable for restraining the apparatus 125 against a region of a body 110. As depicted in FIGS. 1A and 1B, the apparatus is designed for reversible attachment to the region of the body 110 surrounding the medical site 105 and including the medical site 105.

Figure 2B:
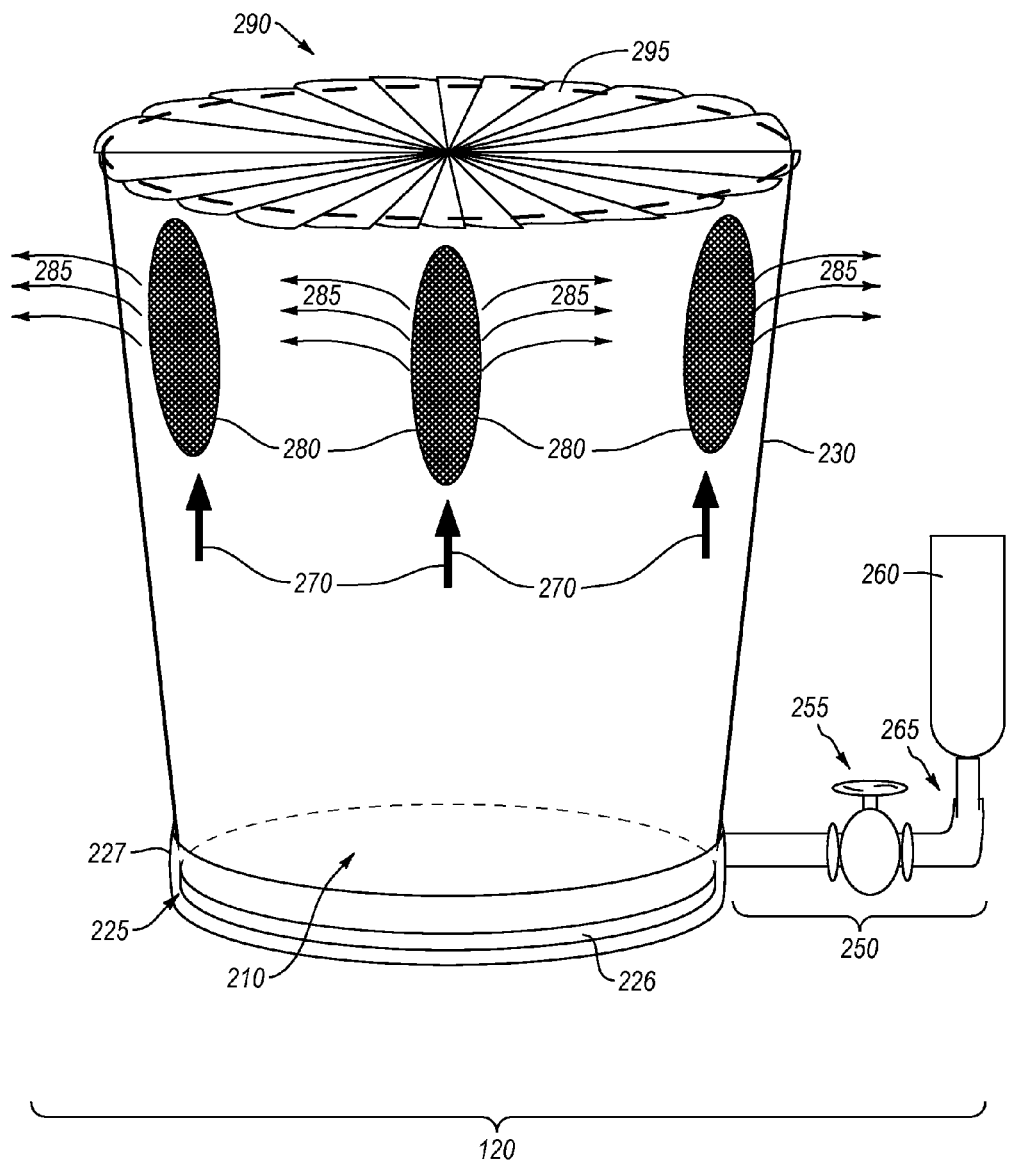

FIG. 2 depicts an embodiment of an apparatus 120 such as those described herein. As shown in FIG. 2, an apparatus 120 includes a structure 230 encompassing an area of space and, when positioned at a region of a body 110, including an isolation field 125. An "isolation field," (identified as 125) as used herein, includes a region of a surface of a body 110 encircled by an apparatus 120 as well as the adjacent space within the structure 230. Although the structure 230 is depicted in FIG. 2 as including a single curvilinear side wall, in some embodiments there may be a plurality of walls. For example, a structure 230 may include a plurality of walls oriented in parallel, forming layers of walls relative to the exterior of the structure 230. For example, a structure 230 may be configured in a square or rectangular shape, and include a plurality of walls oriented at angles less than 180 degrees relative to each other. The structure 230 may be fabricated from a substantially shape retaining material. The structure 230 may be fabricated from a substantially shape retaining material, such as a rigid plastic material, for example polystyrene.

Surfaces of the apparatus 120, including internal surfaces, may be substantially sterile prior to use of the apparatus 120. The structure 230 may be fabricated from a material suitable for sterilization by ultraviolet ("UV") irradiation. UV irradiation includes exposure to electromagnetic radiation of a wavelength between approximately 10 nm and approximately 400 nm. For example, the structure 230 may be fabricated from a UV-resistant plastic, or a plastic including a UV blocking or UV absorbing agent (e.g. an ultraviolet light absorber, or an antioxidant). For example, the structure 230 may include an agent such as benzophenone. The structure 230 may be fabricated from a material suitable for sterilization by ionizing radiation. For example, structure 230 may be fabricated from a material suitable for sterilization by gamma irradiation. Gamma irradiation includes exposure to electromagnetic radiation of frequencies above approximately $10^{19}$ Hz. For example, the structure 230 may be fabricated from a plastic that substantially maintains its structural integrity after exposure to gamma irradiation for some duration of time sufficient to substantially sterilize the structure. For example, the structure 230 may be fabricated, from polycarbonate. The structure 230 may be fabricated from a material suitable for autoclaving, for example, aluminum or stainless steel. The structure 230 may be fabricated from a material suitable for chemical sterilization.

Surfaces of the apparatus 120, including internal surfaces, may be include one or more agent configured to retard growth and/or spread of infection at a medical site 105 prior to use of the apparatus 120. The structure 230 may include one or more anti-microbial or anti-infective agent. For example, the structure 230 may contain an antibiotic compound, or a silver-containing compound, integral to the structure 230 or on a surface of the structure 230. For example, the structure 230 may include one or more anti-microbial or anti-infective agent, integral to the structure 230 or on a surface of the structure 230, in the region of the engagement surface 225. For example, the structure 230 may contain an antibiotic compound or a silver-containing compound on the surface of the engagement surface, or on the surface of the structure adjacent to the engagement surface 225. For example, the structure 230 may contain triclosan. Other examples of anti-microbial and anti-infective agents suitable for use integral to an apparatus 120 or on a surface of an apparatus 120 are described herein.

Although the structure 230 is depicted as a circular column in FIG. 2, the particular shape and configuration of the apparatus 120 and structure 230 may vary depending on the embodiment. For example, while the apparatus 120 is shown here as having a circular cross-section for purposes of illustration, a variety of other shapes may be implemented. For example, an apparatus 120 including a structure 230 may be fabricated of a size and shape with an engagement surface 225 of an oval, oblong, square, rectangular, or other shape as suitable for the embodiment. For example, an apparatus 120 including a structure 230 may be fabricated of a size and shape with an engagement surface 225 configured to conform to an average adult human forearm, abdominal region, thigh region, ankle or other body region as appropriate to the embodiment. In some cases, the region of the body may be substantially planar, such as a region of an abdomen. In other cases, the region of the body may include substantially non-planar sections, such as bent joints, a neck, or an appendage. The configuration of the engagement surface 225 may be adapted specifically for each case or may be of a type that conforms adequately for most applications. Although the engagement surface 225 depicted in FIG. 2 is substantially flat, in some embodiments it may be curvilinear, flexible, or bendable as desired to improve contact of the engagement surface 225 with the region of the body 110 surrounding a medical site 105. In some embodiments the engagement surface 225 may be curved or curvilinear to best conform to the surface of a region of an individual body. See, for example U.S. Pat. No. 3,692,024 to Von Otto, titled "Surgical Appliance," which is herein incorporated by reference.

As depicted in FIG. 2, an apparatus 120 includes an engagement surface 225. An engagement surface 225 is configured to reversibly engage with a surface of a region of a body 110, and to substantially prevent flow of material between the surface of the apparatus 120 and the surface of the region of the body 110. For example, an engagement surface 225 is configured to reversibly engage with a surface of a region of a body 110, and to substantially prevent flow of gas between the apparatus 120 and the surface of the region of the body 110. For example, an engagement surface 225 is configured to reversibly engage with a surface of the individual body region 110, and to substantially prevent flow of contaminants between the surface of the apparatus 120 and the surface of the region of the body 110. For example, an engagement surface 225 is configured to reversibly engage with a surface of the region of the body 110, and to substantially prevent flow of debris between the surface of the apparatus 120 and the surface of the region of the body 110. An engagement surface 225 may be configured to engage with the surface of a specific region of an individual body, for example the surface of the abdomen or forearm. For example, an engagement surface 225 may be configured to engage with a specific region of an average adult human body. For example, an engagement surface 225 may be configured to engage with a specific region of an adult human body of standard proportions.

An engagement surface 225 may be configured to seal to the surface of the region of the body 110. The type of seal may be adapted specifically for each embodiment, or a seal may be of a type that is adequate for many embodiments. An engagement surface 225 may include at least one adhesive 226. For example, an engagement surface 225 may include at least one adhesive 226 on the surface of the engagement surface 225 wherein the at least one adhesive 226 is positioned to reversibly adhere a storage cover 227 over the engagement surface 225. For example, an engagement surface 225 may include at least one adhesive 226 on the surface of the engagement surface 225 wherein the at least one adhesive 226 is positioned to reversibly adhere the engagement surface 225 to the surface of the region of the body 110 substantially surrounding the medical site 105. For example, an engagement surface 225 may include a specific reversible sealing region 220, wherein the reversible sealing region 220 includes an adhesive 226. An engagement surface 225 may include at least one suction device 228. For example, an engagement surface 225 may include at least one suction device 228 positioned to reversibly adhere a storage cover 227 over the engagement surface 225. For example, an engagement surface 225 may include at least one suction device 228 positioned to reversibly adhere the engagement surface 225 to a surface of the region of the body 110 substantially surrounding a medical site 105.

An engagement surface 225 may include an element that predominately comes into contact with a surface of a region of a body 110. For example, an engagement surface 225 may include a reversible sealing region 220. A reversible sealing region 220 may include at least one adhesive positioned to reversibly attach the engagement surface 225 of the apparatus 120 to a region of the body 110. The adhesive properties of an engagement surface 225, for example in a reversible sealing region 220, may be provided by an applied adhesive such as a liquid or spray adhesive. The adhesive may be a chemical adhesive. Suitable adhesives include those that are utilized for medical purposes. For example, the engagement surface 225, for example in a reversible sealing region 220, may include a single-sided adhesive film, a double-sided adhesive film, a spray adhesive, a liquid adhesive, or a gel adhesive. For example, the engagement surface 225, for example in a reversible sealing region 220, may include pressure-sensitive adhesives such as those used to adhere medical devices to a skin surface. Examples include silicone-based adhesives, polyisobutylene, resin emulsion adhesives (such as vinyl acetate resin, acrylic ester copolymer, vinyl acetate/dioctyl maleate copolymer, and acrylic polymer), acrylics, synthetic rubbers, natural rubbers, silicones and block copolymers. See, for example, US Patent Applications Nos. 2007/0208141, 2009/0298999, 2009/0240000, 2009/0163661 and 2009/0247704 to Shull et al., titled "Modified Acrylic Block Copolymers for Hydrogels and Pressure Sensitive Wet Adhesives," which are herein incorporated by reference. See, for example, "Silicone Adhesives in Healthcare Applications," Thomas, published by DOW Corning (2003), which is herein incorporated by reference. The adhesive may provide a substantial bond to a surface of the region of the body 110. For example, the adhesive may include cyanoacrylate-based adhesives such as 2-octyl cyanoacrylate (examples are sold under trade names including LiquiBand®, SurgiSeal™ and DermaBond®). For example, the adhesive may include an albumin glutaraldehyde containing adhesive, (e.g. sold under the trade name BioGlue®). See U.S. Pat. No. 5,385,606 to Kowanko, titled "Adhesive Composition and Method," which is herein incorporated by reference. See "BioGlue: a Review of the Use of this New Surgical Adhesive in Thoracic Surgery," Passage et al., *ANZ Journal of Surgery*, Vol. 75, pages 315-318 (2005), which is herein incorporated by reference. See also the product Skin Tite®, available from Smooth-On Inc., Easton Pa. The "Skin Tite® Product Overview" brochure from Smooth-On Inc., with the company identification "090208" is herein incorporated by reference. The adhesive may be a non-chemical adhesive.

The adhesive properties of the engagement surface 225, for example in a reversible sealing region 220, may include microstructure of the surface. For example, the surface of an engagement surface 225, for example in a reversible sealing region 220, may include microprotrusions. See, for example, US Patent Application Nos. 2005/0181170 to Fearing and Setti, titled "Adhesive Microstructure and Method of Forming Same," 2005/0148984 to Lindsay et al., titled "Gecko-like Fasteners for Disposable Articles," and 2005/0271869 to Jackson titled "Hierarchially-Dimensioned Microfiber-Based Dry Adhesive Materials," which are herein incorporated by reference. See also US Patent Application No. 2008/0169059 to Messersmith et al., titled "Biomimetic Modular Adhesive Complex: Materials, Methods and Applications Therefore," which is herein incorporated by reference.

The adhesive properties of an engagement surface 225, for example in a reversible sealing region 220, may include a conditionally-dependent adhesive. An adhesive may be of a type that is activatable at the onset of use, such as by mixing a plurality of compounds or by the addition of energy such as thermal energy. Examples include modified 1-4-polybutadiene and stimuli-responsive materials. See U.S. Pat. Nos. 5,232,702 to Pfister, titled "Silicone Pressure Sensitive Adhesives for Transdermal Drug Delivery Devices and Related Medical Devices," and 5,603,947 to Wong, titled "Method and Device for Providing Nicotine Replacement Therapy Transdermally/Transbuccally," which are herein incorporated by reference. An engagement surface 225, for example in a reversible sealing region 220, may include an adhesive with temperature-dependent adhesive properties. See, for example, Khongtong and Ferguson, "A Smart Adhesive Joint: Entropic Control of Adhesion at a Polymer/Metal Interface," *JACS Communications*, Vol. 124, pages 7254-7255 (2002), which is herein incorporated by reference. See also Mendes, "Stimuli-responsive Surfaces for Bio-applications," *Chemical Society Reviews*, Vol. 37, No. 11, pages 2512-2529 (2008), which is herein incorporated by reference. An engagement surface 225, for example in a reversible sealing region 220, may include an adhesive with switchable adhesion. See, for example, Vogel and Steen, "Capillarity-Based Switchable Adhesion," *PNAS* Vol. 107, No. 8, pages 3377-3381 (2010), which is herein incorporated by reference.

An engagement surface 225, for example in a reversible sealing region 220, may include a suction device configured to reversibly attach the engagement surface 225 of the apparatus 120 to a surface of the region of the body 110. For example, an engagement surface 225, for example in a reversible sealing region 220, may include a suction device including a flexible device configured to provide lower internal pressure than external pressure and therefore elicit adherence to a skin surface. A suction device may include, for example, a flexible plastic or rubber edge including a concave region configured to provide reduced internal pressure on the skin surface.

An engagement surface 225 may include at least one aperture 210. As illustrated in FIG. 2, a region of the engagement surface 225 positioned within the reversible sealing region 220 may include an aperture 210. In some embodiments, an engagement surface 225 of a structure 120 may include a plurality of apertures. Depending on the embodiment, an aperture 210 may be of a variety of shapes and sizes relative to the shape and size of the engagement surface 225 and relative to the shape and size of a reversible sealing region 220. The aperture 210 may be of a size and shape configured to include the medical site 105 when the apparatus 120 is placed on a region of a body 110. The aperture 210 may be of a size and shape configured to surround the medical site 105 when the apparatus 120 is placed on the region of the body 110. The aperture 210 may be of a size and shape configured to encircle the medical site 105 when the apparatus 120 is placed on the region of the body 110. The aperture 210 may be of a size and shape configured to include the medical site 105 within the aperture 210 when the apparatus 120 is placed on the region of the body 110. The aperture 210 may be of a size and shape configured to include the medical site 105 and a portion of the region of the body 110 within the aperture 210 when the apparatus 120 is placed on the region of the body 110.

As depicted in FIG. 2, an apparatus 120 includes at least one gas port 250. A gas port 250 may include at least one flow meter coupled to the at least one gas port 250. A gas port 250 may include at least one inlet valve 255. An inlet valve 255 may be positioned to regulate gas flow into the gas port 250. An inlet valve 255 may be configured to reversibly block gas flow into the gas port 250. An inlet valve 255 may include a pressure regulator. An inlet valve 255 may include a filter, such as a filter oriented to substantially reduce particulate matter within the gas flowing through the inlet valve 255. An inlet valve 255 may include a filter, such as a filter configured within the inlet valve 255 to substantially sterilize the gas flowing through the inlet valve 255. An inlet valve 255 may be configured to release gas to the gas inlet 240 in response to a triggering event. An inlet valve 255 may be configured to release gas to the gas inlet 240 in response to use of the apparatus 120. For example, an inlet valve 255 may be configured to release gas when pressure is applied to the engagement surface 225. For example, an inlet valve 255 may be configured to release gas when a cover is removed from the engagement surface 225. For example, an inlet valve 255 may be configured to release gas when a switch is moved by a user of the apparatus 120. An inlet valve 255 may be configured to release gas to the gas inlet 240 in response to an electronic controller (e.g. see FIG. 6 and FIG. 7). In some embodiments, an apparatus 120 may include a plurality of gas ports 250, wherein each of the plurality of gas ports are configured with different functionality from the remainder of the plurality of gas ports. In some embodiments, an apparatus 120 may include a plurality of gas ports 250, wherein the plurality of gas ports are positioned distally on the apparatus 120.

As depicted in FIG. 2, an apparatus 120 may include an external gas source 260 configured to be coupled to the at least one gas port 250. A gas port 250 may include a connection region 265 configured for attachment of an external gas source 260 to the gas port 250. A gas port 250 may include a repeatably detachable connector. A gas port 250 may, include conventional releasable gas connectors. A gas port may include a connection region 265 configured for attachment of multiple gas sources to the gas port 250. A gas port 250 may include a connection region 265 configured to vary the relative flow rates of gas from different gas sources, for example a connection region 265 including at least one valve. A gas port 250 may include a connection region 265 configured to vary the relative flow rates of gas from different gas sources, for example a connection region 265 including at least one switch. A gas port 250 may include a connection region 265 configured to vary the relative flow rates of gas from different gas sources in response to an electronic controller (e.g. see FIG. 6 and FIG. 7).

An external gas source 260 may include a container configured to provide stored gas. An external gas source 260 may include a container of compressed gas such as depicted in FIG. 2. A container of compressed gas may be of a variety of sizes, depending on the embodiment. A container of compressed gas may be configured to be portable or to be substantially stationary. For example, a small and portable container of compressed gas may be suitable in many embodiments wherein portability and modest weight are desirable. For example, a large container of compressed gas may be suitable in embodiments intended for situations where easy portability is less of a concern. A container of gas may be fabricated from a material including a metal or a plastic, may be configured to be readily refilled, and may hold the gas in a compressed form. An external gas source 260 may include a gas system, such as a system built into a medical facility or vehicle (e.g. an ambulance or a medical helicopter). For example, an external gas source 260 may include gas originating from a building-based gas system. For example, an external gas source 260 may include gas stored in a gas storage unit configured for multiple gas ports to be connected simultaneously. In some embodiments, a compressor may be utilized to provide a continuous supply of gas. An apparatus 120 may include at least one flow meter coupled to the at least one gas port 250, wherein the at least one flow meter is configured to quantify the flow of gas through the gas port from the external gas source 260. An apparatus 120 may include at least one pressure regulator coupled to the at least one gas port 250, wherein the at least one pressure regulator is configured to control the pressure of the flow of gas through the gas port from the external gas source 260.

A gas source may also include a gas source configured to be internal to the apparatus 120. For example, the gas source may be a region of the structure 230. For example, the structure 230 may include multiple walls, and gas may be stored in a region between the walls. For example, the gas source may be a region of the structure 230. For example, the structure 230 may include a gas storage unit.

Although a single gas source 260 is depicted in FIG. 2, some embodiments may include multiple gas sources. For example, a gas port 250 may include a connection region 265 configured for attachment of two or more gas sources to the gas port 250. Correspondingly, a gas port 250 may include one or more valves configured for regulating the flow of gas from the two or more gas sources through the gas port 250. Although not illustrated in FIG. 2, in some embodiments an apparatus 120 may include a plurality of gas ports. In embodiments wherein an apparatus 120 includes a plurality of gas ports, the gas ports may be configured for attachment to different types of gas sources (e.g., a container of compressed gas and a compressor unit). In embodiments wherein an apparatus 120 includes a plurality of gas ports, the gas ports may be configured to be used in combination or singly. For example, the plurality of gas ports may be configured to enable the flow of gas through a single gas port 250 at any given time. For example, the plurality of gas ports may be configured to enable the flow of gas through multiple gas ports at any given time. An apparatus 120 may include at least one flow meter (not shown in FIG. 2) coupled to the at least one gas port 250. The at least one flow meter may be configured to quantify the flow of gas through the gas port from at least one of the two or more gas sources. The at least one flow meter may be configured to quantify the relative flow of gas from a plurality of gas sources.

The gas provided by the gas source 260 may be of a number of types, depending on the embodiment. For example, the gas source 260 may be configured to provide sterilized gas. For example, the gas source 260 may be configured to provide humidified gas. For example, the gas source 260 may be configured to provide dehumidified gas. For example, the gas source 260 may be configured to provide microcidal or microstatic gas. For example, the gas source 260 may be configured to provide medicinal gas. In some embodiments, the gas may include at least one medicinal compound. In some embodiments, the gas may include at least one anti-microbial compound. In some embodiments, the gas may include at least one microcidal compound. In some embodiments, the gas may include at least one antiseptic compound. In some embodiments, the gas may include at least one anesthetic compound. In some embodiments, the gas may include at least one microstatic compound. Depending on the embodiment, the gas may include at least one compound previously identified as a healing-promotive or healing-accelerating compound. The gas supplied may be any mixture of components appropriate for the embodiment, which may include but are not limited to nitrogen-, oxygen-, and carbon-containing gasses. For example, the gas source 260 may be configured to provide air. For example, the gas source 260 may be configured to provide carbon dioxide gas. For example, the gas source 260 may be configured to provide nitrogen gas. Nitrogen gas may, for example, be desirable for use in embodiments wherein fire is a concern. Nitrogen gas may, for example, be desirable for use in embodiments wherein chemical reactions are a concern. For example, an oxidation reaction, such as may be a concern with white phosphorus exposure, may be suppressed in the presence of nitrogen gas. For example, the gas source 260 may be configured to provide oxygen gas. The gas provided by the gas source 260 may be, for example, of a type previously identified as inhibiting bacterial growth. The gas source 260 may be configured to provide microcidal gas. See, for example, Ogata and Shibata, "Protective Effect of Low-Concentration Chlorine Dioxide Gas Against Influenza A Virus Infection," Journal of General Virology, Vol. 89, pages 60-67, (2008), which is herein incorporated by reference. The gas source 260 may be configured to provide microstatic gas. The gas source 260 may be configured to provide medicinal gas. See, for example, U.S. Pat. No. 6,810,288 to Joshi, titled "Device and Method for Wound Healing and Control," which is herein incorporated by reference. See, for example, U.S. Pat. No. 6,494,858 to van der Linden, titled "Method and Device for Producing an Atmosphere in a Region, and Use of Carbon Dioxide for the Manufacture of a Medicament," which is herein incorporated by reference. See, for example, U.S. Pat. No. 6,179,804 to Satterfield, titled "Treatment Apparatus for Wounds," which is herein incorporated by reference.

The gas provided by the gas source 260 may be humidified or dehumidified. The gas source 260 may be configured to provide humidified gas. Humidified gas may contain a partial pressure of water vapor higher than the ambient atmospheric pressure in the region exterior to the apparatus 120. For example, humidified gas may be desirable for embodiments intended for medical uses to reduce skin irritation and dehumidification of a medical site. For example, humidified gas may be desirable for embodiments intended for medical uses to promote wound healing. The gas source 260 may be configured to provide dehumidified gas. Dehumidified gas may contain a partial pressure of water vapor lower than the ambient atmospheric pressure in the region exterior to the apparatus 120. For example, dehumidified gas may be desirable for embodiments wherein the medical site includes a chemical agent that may react with the water vapor in the gas and therefore promote an undesirable chemical reaction. For example, in embodiments where sodium or magnesium burns are of concern (e.g. industrial embodiments or chemical laboratories), dehumidified air may be desirable to mitigate potential reactions between the chemicals on the surface of a region of a body and water vapor in the gas. For example, dehumidified gas may be desirable for embodiments wherein the medical site includes a pathogen, such as a bacterial agent, fungus or mold with growth characteristics that may be minimized in a low-water environment.

In some embodiments, the gas source 260 may be configured to provide gas at a temperature below the ambient temperature of the apparatus 120. For example, an external gas source 260 may include a canister of compressed gas at ambient temperature of the apparatus 120, wherein the compressed gas is subject to adiabatic cooling due to the configuration of the gas port 250 when the pressure of the gas is reduced at the time of release of the gas from the gas source 260. For example, an external gas source 260 may include a canister of compressed gas retained at a temperature lower than the ambient temperature of the apparatus 120, wherein the gas released from the external gas source 260 retained at a temperature lower than the ambient temperature of the apparatus 120 has a temperature lower than the ambient temperature of the apparatus 120. Gas provided at a temperature below the ambient temperature of the apparatus may be desirable, for example, in embodiments wherein the medical site includes a thermal burn. Gas provided at a temperature below the ambient temperature of the apparatus may be appropriate, for example, in embodiments wherein constriction of blood vessels at the medical site 105 is desirable, such as to mitigate an allergic reaction or to reduce blood loss. For example, constriction of blood vessels at the medical site 105 may be desirable during surgery or following injury.

An apparatus 120 includes one or more gas inlets 240 operably attached to the gas port 250, the one or more gas inlets 240 oriented to maintain a non-turbulent gas flow 245 traversing at least a part of the surface on the individual body. An apparatus 120 includes one or more gas inlets 240 operably attached to the gas port 250, the one or more gas inlets 240 oriented to maintain a non-turbulent gas flow 245 in parallel with at least a part of the surface on the individual body. Some embodiments may include a plurality of gas inlets 240. The apparatus 120 may include at least one gas supply duct operably connected to the at least one gas port and the plurality of gas inlets. The one or more gas inlets 240 are oriented to maintain a non-turbulent gas flow 245 traversing at least a part of the surface on the individual body. For example, as depicted in FIG. 2, the gas inlets 240 may be oriented to maintain a non-turbulent gas flow 245 traversing parallel to the surface of the region of the body 110 encompassed by the opening of the engagement surface 225.

As used herein, "non-turbulent gas flow" refers to gas flow that includes minimal recirculation and eddies in the flow of the gas. The non-turbulent gas flow from the gas inlets 240 may be, for example, directed to substantially remove free particulate matter (including contaminants and pathogenic particulate matter) from the surface on the individual body. See, for example, gas flow labeled with identifier 245 in FIG. 2. The non-turbulent gas flow from the gas inlets 240 may be, for example, directed to substantially direct free particulate matter towards one or more gas outlets 280 and any associated filter units configured to entrap particulate matter. See, for example, gas flow labeled with identifier 270 in FIG. 2. Generally, non-turbulent gas flow is associated with a small Reynolds number. For example, non-turbulent gas flow is generally associated with Reynolds numbers of 10 or less. Particulate matter is substantially moved with the direction of gas flow away from the surface on the individual body. Particulate matter moved with the direction of gas flow away from the part of the surface on the individual body may be further removed from the isolation field by becoming associated with a filter associated with a gas outlet 280. For example, a filter may be integral to a gas outlet 280. For example, particulate matter moving with the direction of gas flow away from the region 110 of the surface on the individual body may substantially follow the gas flow away from the surface of the body and into the material of one or more filters associated with a gas outlet 280 as the gas flows outward from the structure through a gas outlet. In some contexts, "non-turbulent" gas flow may be considered "laminar" gas flow, "streamline" gas flow, or "smooth" gas flow.

As used herein, "particulate matter" includes macroscopic, microscopic and nanoscopic particules, including pathogens. For more information on the relative sizes of some pathogens (including viruses, bacteria and fungi), see Kowalski and Bahnfleth, "MERV Filter Models for Aerobiological Applications," *Air Media*, pages 13-17 (summer 2002), which is herein incorporated by reference. Particulate matter may include contaminating material. For example, particulate matter may include contaminating material such as metal, wood or plastic. Particulate matter may include shrapnel, shells, shot or fragments thereof. Particulate matter may include chemical fragments, such as fragments of a chemical compound. Particulate matter may include wound debris. For example, particulate matter may include tissue fragments.

The one or more gas inlets 240 may be oriented to maintain a streamline gas flow traversing at least a part of the surface on the individual body. The one or more gas inlets 240 may be oriented to maintain a streamline gas flow in parallel with at least a part of the surface on the individual body. The one or more gas inlets 240 may be oriented to maintain a laminar flow of gas traversing at least a part of the surface on the individual body. The one or more gas inlets 240 may be oriented to maintain a laminar flow of gas in parallel with at least a part of the surface on the individual body. See, for example, "Historical Usage of Laminar Airflow," from the Germfree Corporation, Ormond Beach Fla., which is herein incorporated by reference. See, for example, U.S. Pat. No. 3,252,400 to Madl, titled "Means Providing a Coordinated Air Flow in an Enclosure," which is herein incorporated by reference. See, for example, Masliyah, "On Laminar Flow in Curved Semicircular Ducts," *Journal of Fluid Dynamics*, Vol. 99, part 3, Pages 469-479 (1980), which is herein incorporated by reference. The one or more gas inlets 240 may be configured to preserve the integrity of the non-turbulent gas flow 245 traversing at least a part of the surface on the individual body wherein the at least a part of the surface on the individual body includes a non smooth surface. For example, the surface on the individual body may include a medical site such as a wound that creates an obstruction to the non-turbulent gas flow 245. For example, the surface on the individual body may include debris that creates an obstruction to the non-turbulent gas flow 245. The non-turbulent gas flow 245 is oriented by the one or more gas inlets 240 in a manner to substantially direct the overall flow of particulate matter away from the medical site 105. For example, the overall flow of particulate matter may be directed by the non-turbulent gas flow over the surface of the medical site 105 and then to a position away from the medical site 105 (e.g. as illustrated in FIG. 2 as gas flows 245 and 270). See, for example, U.S. Pat. No. 4,412,849 to Shahani, titled "Method and Apparatus for Control of Gas-Borne Particulates," which is herein incorporated by reference. See, for example, U.S. Pat. No. 4,860,643 to Spearow, titled "Ventilated Clean Room Work Station with Aerodynamic Exhaust Baffle," which is herein incorporated by reference.

In various embodiments, the gas flow through an apparatus 120 may be modeled using standard computation techniques. See, for example, the "Fluid Flow Simulation" validation module available with SolidWorks® Premium 2010, available from Dassault Systemes SolidWorks Corporation, Concord Mass., the "Product Description" brochure for which with the company identifier MKPREMDSENG0609 is herein incorporated by reference. The modeling of the gas flow through an embodiment of an apparatus 120 may be desirable, for example, during the design phase in order to ensure that non-turbulent gas flow is expected during use of the apparatus 120.

The one or more gas inlets 240 may be operably attached to a tubular component. For example, the one or more gas inlets 240 may be operably attached to a gas supply duct 235. The engagement surface 225 may include a connector positioned to place a tubular component operably attached to the one or more gas inlets 240 within the structure 230. The engagement surface 225 may include a connector positioned to place a tubular component operably attached to the one or more gas inlets 240 adjacent to the surface of the individual body (e.g. the region of the individual body 110). The engagement surface 225 may include a connector positioned to place a tubular component operably attached to the one or more gas inlets 240 distal to the surface of a region of the individual body. The gas inlets 240 may be connected to the gas port 250 by a gas supply duct 235. Although the gas supply duct 235 is illustrated in FIG. 2 as a circular shape, the shape of the gas supply duct 235 may vary depending on the embodiment. As depicted in FIG. 2, a gas supply duct 235 may be integral to the structure 230, such as being a distinct tubular component integral to the structure 230. For example, a gas supply duct 235 may include a tubular duct fixedly attached to the structure 230. For example, a gas supply duct 235 may include a substantially tubular duct operably attached to the structure 230. For example, a gas supply duct 235 may include a space within layers of the wall of the structure 230, wherein the layers are configured to form a duct-like structure. A gas supply duct 235 may include one or more filters. The one or more filters may be configured to substantially block the ingress of particulate matter into the structure 230. The one or more filters may be configured to substantially block the ingress of particulate matter into the structure 230. The one or more filters may be configured to substantially block the ingress of certain materials into the structure 230.

Depending on the embodiment, filters may be positioned in multiple places in an apparatus. One or more filters may, for example, be positioned to filter gas flow through a gas port 250. One or more filters may be integral to a gas port 250. One or more filters may, for example, be positioned to filter gas flow through a gas inlet 240. One or more filters may be integral to a gas inlet 240. One or more filters may, for example, be positioned to filter gas flow through a gas outlet 280. One or more filters may be integral to a gas outlet 280.

"Filters," as used herein, includes filters which capture impurities within the gas with the effect of removing the impurities from the gas. Filters may remove, for example, particulate matter from the gas as the gas flows through the filter. Particulate matter may be of a variety of sizes down to the micron scale. Particulate matter may include, for example, dust, debris, blood, or wound fragments at the macroscopic or microscopic scale. Such removal may substantially sterilize a gas that has passed through the filter. The filters may include filters with multiple layers. Filters including multiple layers may include filters wherein the layers are configured to act in concert or subsequently to generate the entirety of the filtering effect. Filters including multiple layers may include filters wherein the layers are configured to act in concert or subsequently to substantially remove impurities from gas flow. The one or more filters may include a material such as, but not limited to, polytetrafluorethylene or polyvinyledene fluoride. See, for example, the Emflon® and Emflon II® containing filters as well as HDC® II containing filters sold by Pall Corporation, headquartered in Port Washington N.Y. The Pall Corporation product brochure for the "HDC® II Filter Cartridges for Gas Applications," dated May 23, 2010, is herein incorporated by reference. The Pall Corporation product brochure for the "Emflon® PFA Filter Cartridges" dated May 23, 2010, is herein incorporated by reference. The Pall Corporation product brochure for the "Acro® 50 Vent Devices with Emflon II® Membrane," downloaded from Pall Corporation on May 21, 2010 is incorporated herein by reference. The filters may include "high efficiency particulate arresting" (sometimes referred to as 'high efficiency particulate air") ("HEPA")-type filters. The filters may be designed to remove 99.97% of gasborne particles measuring 0.3 microns or larger in diameter passing through the filters. The filters may substantially sterilize gas passing through the filters. The filters may include "ultra low particulate air" ("ULPA")-type filters. The filters may be designed to remove 99.999% of gasborne particles measuring 120 nanometers or larger in diameter passing through the filters. For more information regarding filter performance in the 0.3 to 10 micron size range, and the relative sizes of common pathogens to filter performance, see Kowalski and Bahnfleth, ibid., which is herein incorporated by reference. See also Whitt, "Air Filtration and the Use of HEPA Filters in Biological Safety Cabinets," published by Nuaire Corporation, Plymouth Minn., downloaded on Mar. 19, 2010. In some embodiments, a filter may include a high efficiency gas absorption (HEGA) filter. HEGA filters may be particularly desirable in embodiments intended for use wherein the medical site includes chemical contaminants. One or more filters may include electrostatic components. One or more filters may include an adsorbing material, such as activated charcoal, carbon aerogel, silica gel, or zeolites.

The one or more filters may include filters configured to capture viral particles. The one or more filters may include filters configured to remove viral particles. See, for example, Roelants, "Evaluation of a Commercial Air Filter for Removal of Viruses from the Air," *Applied Microbiology*, Vol. 16, No. 10, (1968), which is herein incorporated by reference. The one or more filters may include filters configured to capture and remove one or more fungal contaminants, for example spores or fungal bodies. The one or more filters may include filters configured to capture microbial particles. The one or more filters may include filters configured to remove microbial particles. The one or more filters may include filters configured to capture bacterial particles. The one or more filters may include filters configured to remove bacterial particles. The one or more filters may include filters configured to capture and remove a contaminating fluid, for example blood. The one or more filters may include filters configured to capture and remove a contaminating gas, for example a nitrogen gas or a hydrocarbon gas. The one or more filters may include filters configured to capture and remove a contaminating liquid, for example, water. A filter may include activated charcoal.

Although the one or more gas inlets 240 are depicted in FIG. 2 as circular openings, the one or more gas inlets 240 may be of a variety of shapes as appropriate to the embodiment to direct and maintain the non-turbulent gas flow 245. The one or more gas inlets 240 may include flanges, bevels, chamfer elements, baffles, vanes, gas flow guide surfaces, or other physical elements as appropriate to direct and maintain the non-turbulent gas flow 245. In some embodiments, the one or more gas inlets 240 may include one or more air control elements as appropriate to direct and maintain the non-turbulent gas flow 245. In some embodiments, the one or more gas inlets 240 may include one or more gas guide elements as appropriate to direct and maintain the non-turbulent gas flow 245. See, for example, U.S. Pat. No. 6,592,451 to Tang, titled "Fan Unit," which is herein incorporated by reference. In some embodiments, the one or more gas inlets 240 may include one or more atomizer, nebulizer or mist devices. See, for example, Anderson, "History of Aerosol Therapy: Liquid Nebulization to MDIs to DPIs," *Respiratory Care*, Vol. 50, No. 9, pages 1139-1150 (2005) and the associated Discussion, which is herein incorporated by reference.

A gas duct 235, gas port 250, or one or more gas inlets 240 may include one or more devices positioned to provide aerosolized compound into the gas flow. A gas duct 235 may include at least one device operably attached to the gas duct 235, the at least one device configured to introduce aerosol into the non-turbulent gas flow. For example, the device may be configured to release fine droplets into the non-turbulent gas flow from within the gas duct 235. One or more gas inlets 240 may include at least one device operably attached to the one or more gas inlets 240, the at least one device configured to introduce aerosol into the non-turbulent gas flow. A gas port 250 may include at least one device operably attached to the gas port 250, the at least one device configured to introduce aerosol into the non-turbulent gas flow. For example, a gas duct 235, gas port 250, or one or more gas inlets 240 may include a nebulizer configured to provide fine liquid droplets or aerosol to the gas flow. For example, a gas duct 235, gas port 250, or one or more gas inlets 240 may be operably attached to a nebulizer configured to provide fine liquid droplets or aerosol to the gas flow. For example, a gas duct 235, gas port 250, or one or more gas inlets 240 may include an atomizer nozzle configured to provide fine liquid droplets or aerosol to the gas flow. For example, a gas duct 235, gas port 250, or one or more gas inlets 240 may be operably attached to an atomizer nozzle configured to provide fine liquid droplets or aerosol to the gas flow. For example, see U.S. Pat. No. 4,941,618 to Hildebrand and Urh, titled "Nebulizer Employing a Fine Mesh Screen," which is herein incorporated by reference. For example, see the Publication "FloMax® Air Atomizing Nozzles High Efficiency Nozzles Offer Tight Control of Drop Size and Spray Coverage, Provide Precise Performance," which is herein incorporated by reference. FloMax® Air Atomizing Nozzles are available from Spraying Systems Co., Wheaton Ill. For example, see U.S. Pat. No. 4,783,008 to Ikeuchi and Oonishi, titled "Atomizer Nozzle Assembly," which is herein incorporated by reference. A device configured to introduce fine liquid droplets or aerosol into the non-turbulent gas flow may include devices that utilize ultrasonic vibrations to form the fine liquid droplets or aerosol, such as described in U.S. Pat. No. 4,850,534 to Takahashi et al., titled "Ultrasonic Wave Nebulizer," which is herein incorporated by reference. A device configured to introduce fine liquid droplets or aerosol into the non-turbulent gas flow may include devices that are located in the interior of a gas duct 235. See, for example, US Patent Application No. 2009/0173341 to Reinhold et al., titled "Inhalation Device Having an Optimized Air Flow Path," which is herein incorporated by reference. A gas duct 235, gas port 250, or one or more gas inlets 240 may be operably attached to one or more reservoirs configured to store one or more compounds for creation of fine droplets or aerosol by one or more devices. A device may incorporate at least one reservoir for compounds integral to the device.

Depending on the embodiment, a variety of compounds may be added to the non-turbulent gas flow. For example, compounds may be added to the non-turbulent gas flow as droplets or aerosols. For example, compounds may be added to the non-turbulent gas flow from one or more devices such as nebulizers or atomizers, wherein the one or more devices are operably connected to a gas duct 235, gas port 250, or one or more gas inlets 240. Similarly, depending on the embodiment, a variety of compounds may be dispensed to the interior of the structure 230 as droplets or aerosols. For example, a variety of compounds may be dispensed to the interior of the structure 230 with spray devices (see, e.g. FIG. 8). Compounds added to the non-turbulent gas flow or dispensed to the interior of the structure may be selected, for example, to promote healing, reduce pathogen viability, provide palliative care to an individual, reduce contamination, improve aesthetics, or a combination thereof. Compounds added to the non-turbulent gas flow or dispensed to the interior of the structure may include, for example, antimicrobial, antiseptic, antifungal and anesthetic agents, or a combination thereof. In some embodiments wherein multiple compounds are added to the non-turbulent gas flow or dispensed to the interior of the structure, compounds may be selected to for compatibility and/or synergistic effects. For example, antibiotic compounds may be included that are effective against different classes of bacteria, and therefore the combination of the compounds synergistically adding a range of antibiotic effectiveness. For example, an anesthetic compound may be included with a healing promoting compound, thereby increasing palliative care while promoting healing. For example, an anesthetic compound may be included with a compound that promotes healing of chemical burns.

One or more compounds may be included in various embodiments for addition to the non-turbulent gas flow, dispensation into the interior of the structure 230, or both. Compounds will be selected depending on the individual embodiment, however representative examples are provided herein. Compounds may include, for example, compounds associated with healing promotion. For example, see U.S. Pat. No. 5,661,132 to Eriksson et al., titled "Wound Healing," which is herein incorporated by reference. For example, compounds may include Dermagran® Moisturizing Spray, manufactured by Derma Sciences with corporate headquarters in Princeton, N.J. For example, compounds may include Granulex® Cleanser Spray, available from UDL Laboratories, with corporate headquarters in Rockford, Ill. For example, compounds may include CothiVet® Topical Wound Spray. For example, the compounds may include one or more hydrogels for use on wounds. See, for example, U.S. Pat. No. 7,083,806 to Rippon and Meadows, titled "Wound Gels," which are herein incorporated by reference. Compounds may include, for example, antimicrobial, antiseptic, antifungal and anesthetic agents, or a combination thereof. For example, see Matsumoto et al., "Antibiotic Topical Spray Applied in a Simulated Combat Wound," *Arch. Surg.* Vol. 95, pages 288-294 (1967), which is herein incorporated by reference. For example, a gentamicin sulfate with betamethasone valerate composition may be used in some embodiments (for example, Betagen™, GenOne™, and Gentocin®). For example, a tetracycline containing compound may be used in some embodiments (for example, Terramycin®Wound Spray). For example, an erythromycin and zinc acetate containing compound may be used in some embodiments (for example, Zineryt). For example, a Bacitracin-containing compound may be used in some embodiments. For example, a polymyxin B sulfate and bacitracin zinc containing compound may be used in some embodiments (see, for example, Polysporin®). See, for example, Walton et al., "The Efficacy of Polysporin First Aid Antibiotic Spray (Polymyxin B Sulfate and Bacitracin Zinc) Against Clinical Burn Wound Isolates," *Journal of Burn Care & Rehabilitation*, Vol. 12, Pages 116-119 (1991), which is herein incorporated by reference. For example, a sulfa-drug containing compound may be used in some embodiments (e.g. a 5% mafenide acetate solution, available as, for example, Sulfamylon®). For example, the compound may include an antibiotic in a carrier compound. See, for example, U.S. Pat. No. 5,905,092 to Osborne and Yang, titled "Topical Antibiotic Composition Providing Optimal Moisture Environment for Rapid Wound Healing that Reduces Skin Contraction," which is herein incorporated by reference. For example, one or more antifungal agents may be used in some embodiments. For example, 1% tolnafate (for example, Tinactin®) may be used in some embodiments. For example, 2% miconazole nitrate (for example, Lotrimin®) may be used in some embodiments. For example, one or more antiseptics may be used in some embodiments. For example, a solution containing iodine may be used in some embodiments (e.g. Scrub Care® Aerosol Spray Iodine Topical Solution). For example, one or more anesthetics may be used in some embodiments (for example, benzethonium chloride, available as Dermoplast® products). For example, at least one combination of antiseptic and anesthetic may be used in some embodiments. For example, a solution containing 0.13% benzalkonium chloride and 1% pramoxine hydrochloride (for example, Neosporin® NEO to Go®) may be used in some embodiments. For example, a solution containing benzalkonium chloride and lidocaine hydrochloride (for example, Bactine® First Aid Spray) may be used in some embodiments. For example, superoxidized water (e.g. Microcyn® OTC Skin and Wound Cleanser) may be used in some embodiments. For example, a silver containing compound may be used in some embodiments. See, for example, U.S. Pat. Nos. 6,551,577 and 6,987,133 to Chen, both titled "Topical Spray for Burn Treatment and Anti-Infection," which are herein incorporated by reference. For example, a glucocorticoid containing compound (e.g. betamethasone dipropionate, available as Diprolene® and DermaZinc™), may be used in some embodiments. For example, a compound containing at least one biological protein, such as Fibroblast Growth factor (e.g. bFGF), Keratinocyte Growth Factor (e.g. KGF), Interleukin (e.g. IL1Beta), and/or Heat Shock Protein (e.g. Hsp90), may be used in some embodiments. See, for example, Kitamura et al., "Periodontal Tissue Regeneration Using Fibroblast Growth factor-2: Randomized Controlled Phase II Clinical Trial," *PLOS One*, Vol. 3, Issue 7, pages 1-11, (2008), which is herein incorporated by reference. For example, Repifermin (KGF-2) may be used in some embodiments. For example, at least one interleukin-containing compound may be used in some embodiments. For example, at least one heat shock protein containing compound may be used in some embodiments. See, for example, US Patent Application No. 2010/0035815 to Li et al., titled "Skin Wound Healing Compositions and Methods of Use Thereof," which is herein incorporated by reference. Compounds may include, for example, compounds including one or more thrombins, for example in embodiments wherein it is desirable to reduce blood loss from a wound or surgical site. See, for example, Thrombin-JMI®, available from King Pharmaceuticals, with corporate headquarters in Bristol, Tenn. Compounds may include, for example, compounds containing nucleic acids. For example, compounds may include plasmid DNA in a liposomal formulation. See, for example, Meykadeh et al., "Topical Application of Plasmid DNA to Mouse and Human Skin," *Journal of Molecular Medicine*, Vol. 83, No. 11, pages 897-903 (2005), which is herein incorporated by reference. Compounds may include, for example, compounds associated with altering gene expression in tissue, which may include cosmetic enhancement of the wound region after healing. See, for example, U.S. Pat. No. 7,504,385 to Binetti, titled "Si-RNA-Mediated Gene Silencing Technology to Inhibit Tyrosinase and Reduce Pigmentation," which is herein incorporated by reference. Compounds may include siRNAs, which may be configured to silence local gene expression in the wound tissue or associated pathogens. See, for example, Thanik et al., "Topical Matrix-Based siRNA Silences Local Gene Expression in a Murine Wound Model," *Gene Therapy* Vol. 14, pages 1305-1308 (2007), which is herein incorporated by reference.

An apparatus 120 includes one or more gas outlets 280 distally positioned on the structure 230 from the one or more gas inlets 240, the one or more gas outlets 280 configured to release gas 285 from the isolation field 125 while maintaining positive pressure in the isolation field 125 relative to the outside environment of the structure 230. Positive pressure may be maintained, for example, by balancing the relative ingress of gas through the one or more gas inlets 240, relative to the egress of gas through the one or more gas outlets 280. The positive pressure balance of the apparatus 120 may include gas leakage from regions other than through the one or more gas outlets 280, although the total gas egress from the structure 230 substantially flows through the one or more gas outlets 280. For example, the engagement surface 225 of the apparatus 120 is configured to allow minimal gas leak between the engagement surface 225 and the surface of the region of the body 110. For example, the engagement surface 225 of the apparatus 120 is configured to allow minimal gas leak from the one or more access sites 290. The positive pressure may be maintained on a fixed basis, i.e. based on a fixed ingress flow and egress flow of gas from the structure 230. The positive pressure may be maintained by actively controlling the relative rate of ingress of gas through the one or more gas inlets 240, relative to the relative rate of egress of gas through the one or more gas outlets 280. For example, the relative rate of ingress of gas through the one or more gas inlets 240, relative to the relative rate of egress of gas through the one or more gas outlets 280 may be controlled with an electronic controller (e.g. see FIG. 6 and FIG. 7). For example, the relative rate of ingress of gas through the one or more gas inlets 240, relative to the relative rate of egress of gas through the one or more gas outlets 280 may be manually controlled by controlling the relative rate of ingress of gas through the one or more gas inlets 240, relative to the relative rate of egress of gas. Manual control may be based on gas pressure information from a gauge or meter operably attached to the structure 230.

Positive pressure in the isolation field 125 relative to the outside environment of the structure 230 may improve the prognosis of a medical site. Positive pressure on a wound, for example, has been indicated to reduce blood loss and promote tissue stasis in some situations. See, for example, European Patent Application No. EP 1 008 334 A2 to Kuslich, titled "Apparatus for Establishing and Maintaining a Positive Atmospheric Pressure Surgical Field," which is herein incorporated by reference. See, for example, U.S. Pat. No. 6,199,551 to Kuslich, titled "Apparatus for Establishing and Maintaining a Positive Atmospheric Pressure Surgical Field," which is herein incorporated by reference. See, for example, U.S. Pat. No. 4,550,713 to Hyman, titled "Method and Apparatus for Opposing Deformity, Displacement, and Expulsion of the Ocular Tissues During Open Eye Surgery," which is herein incorporated by reference. Positive pressure within the apparatus 120 may also substantially decrease the flow of contaminants that may be carried by gas flow into the isolation field 125. For example, positive pressure within the apparatus 120 will create net gas flow out of the apparatus 120 in the case of leakage or imperfect seals, and thereby substantially push potentially contaminating material away from the interior of the apparatus 120. For example, positive pressure within the apparatus 120 will create net gas flow out of the apparatus 120 while access to the interior of the apparatus is obtained through an access site, and thereby substantially move potentially contaminating material away from the interior of the apparatus 120. For example, positive pressure within the apparatus 120 will create net gas flow out of the apparatus 120 through an imperfectly sealed access site, and thereby substantially block potentially contaminating material from entering the interior of the apparatus 120. Positive pressure, therefore, may contribute to the isolation of the isolation field from the environment surrounding the apparatus 120.

It is envisioned that the overall flow of gas within the apparatus 120 will be in a direction from the one or more gas inlets 240, traversing (depicted as 245) at least a part of the surface on the individual body, in a direction (depicted as 270) to a region distal to the gas inlets 240, toward the one or more gas outlets 280 and finally out (depicted as 285) of the structure 230. The one or more gas outlets 280 may include one or more filters configured to filter the gas (depicted as 285) released from the structure 230. The one or more gas outlets 280 may include one or more filters configured to substantially sterilize the gas released from the isolation field. The one or more gas filters configured to substantially sterilize the gas released from the isolation field may include at least one of: polytetrafluoroethylene, and polyvinyledene fluoride. The one or more filters configured to substantially sterilize the gas released from the isolation field may include at least one HEPA filter material. The one or more gas outlets 280 may include a particulate filter. The particulate filter may be configured to substantially block particulate matter from release with gas released from the isolation field.

As illustrated in FIG. 2, the structure 230 includes at least one sealable access site 290. The at least one sealable access site 290 is configured to allow one or more human fingers or medical instruments to access the interior of the structure 230 while substantially maintaining positive pressure within the structure 230. The at least one sealable access site 290 is configured to substantially seal around one or more human fingers or medical instruments inserted through the sealable access site. The at least one sealable access site 290 is configured to remain closed until accessed from a region external to the apparatus 120. For example, a sealable access site 290 may be configured to remain closed until insertion of a human finger or medical instrument through the sealable access site 290. The at least one sealable access site 290 is configured to act as a substantial barrier to gas leakage until insertion of a human finger or medical instrument through the sealable access site 290. The at least one access site 290 may be sealable externally, such as with an external cover. The at least one sealable access site 290 may be sealable by operation of the sealable access site 290 itself. For example, as depicted in FIG. 2, in some embodiments the at least one sealable access site 290 may include a mechanical iris structure 295. As depicted in FIG. 2, the at least one sealable access site 290 may include a mechanical iris structure 295 including a plurality of partially overlapping blades. A mechanical iris structure 295 may be configured to provide access to the interior of the structure 230, such as for a human finger or medical instrument, and then reclosed after access. A mechanical iris structure 295 may be configured to provide access to the interior of the structure 230 for a human finger or medical instrument while providing a minimal aperture for the access, thus minimizing gas leakage from the sealable access site 290 and, therefore, maintaining positive pressure within the structure 230. Although the mechanical iris structure 295 depicted in FIG. 2 encompasses the entirety of a face of the structure 230, in some embodiments the sealable access site 290 may be smaller than a face of the structure 230.

In some embodiments, the at least one sealable access site 290 may include a seal fabricated from at least one flexible material. The seal may be an external seal, for example a seal configured to reversibly mate with and seal to the exterior of the sealable access site 290. The seal may be an internal seal, such as material within the access site configured to reseal after access is obtained through the sealable access site 290. For example, the at least one sealable access site may include a material such as rubber or latex. The at least one sealable access site 290 may include a seal formed by multiple overlapping pieces of flexible material. For example, the at least one sealable access site 290 may include a seal fabricated from a flexible plastic material. For example, the at least one sealable access site may include a material configured to create a minimal aperture surrounding a human finger or medical instrument inserted through the sealable access site 290, thus minimizing gas leakage from the sealable access site 290 and, therefore, positive pressure within the structure 230. For example, the at least one sealable access site 290 may include a silicone ring configured to substantially remain in contact with the surface of a human finger or medical instrument inserted through the silicone ring. For example, the material of the at least one sealable access site 290 may include an expandable aperture.

The at least one sealable access site 290 may be resealable. The at least one sealable access site 290 may be configured to reseal after access is complete. The at least one sealable access site 290 may include a cover configured to reversibly mate with the exterior of the at least one sealable access site 290. A sealable access site 290 may include a cover configured to mate with the external surface of the sealable access site 290 and therefore substantially block gas leak from the sealable access site 290 after a human finger or medical instrument is removed from the sealable access site 290. For example, a cover may include at least one adhesive configured to substantially block gas leakage between a surface of the cover and an external surface of the sealable access site 290. For example, a cover may include a stretchable material configured to substantially block gas leakage between a surface of the cover and an external surface of the sealable access site 290. For example, a cover may include at least one surface configured to mate with, and substantially block gas leakage between, a surface of the cover and an external surface of the sealable access site 290. A cover may include a tether or non-detaching region and therefore be configured to be continually located adjacent to the structure 230.

As illustrated in FIG. 2, the at least one sealable access site 290 may be fabricated for access through a substantial area relative to a face of the structure 230. In other embodiments, such as those depicted in FIGS. 4, 6, 7, 8 and 9, the at least one sealable access site 290 may be fabricated for access through a limited area relative to a face of the structure 230. For example, the at least one sealable access site 290 may be configured to include only a portion of a face of the structure 230. For example, the at least one sealable access site 290 may be configured to include less than half of the total area of a face of the structure 230. For example, the at least one sealable access site 290 may be configured to include less than a quarter of the total area of a face of the structure 230. For example, the at least one sealable access site 290 may be configured to include a region of a side of the structure 230. For example, the at least one sealable access site 290 may be configured to open over a limited surface area of the entire sealable access site 290. In some embodiments, there are a plurality of access sites 290 which may be separately configured for the insertion of individual human fingers and medical instruments. Although FIG. 2 depicts a sealable access site 290 located on the face of the structure 230 distal to the engagement surface 225, some embodiments may include one or more sealable access sites 290 on the sides of the structure 230 adjacent to the engagement surface 225.

In some embodiments, the at least one sealable access site 290 may be configured for the insertion of one or more human fingers. For example, the at least one sealable access site 290 may be configured in a size and shape sufficient for the insertion of an average-sized adult human finger into the at least one sealable access site 290 to a sufficient depth to come into contact with the medical site 105. The at least one sealable access site 290 may be configured to be closed until insertion of one or more human fingers into the access site 290. The at least one sealable access site 290 may be configured for the insertion of one or more medical instruments. For example, the at least one sealable access site 290 may be configured in a size and shape sufficient for the insertion of one or more medical instruments into the at least one sealable access site 290 to a sufficient depth to come into contact with the medical site 105. For example, the at least one sealable access site 290 may be configured for insertion of a medical instrument such as a scalpel, a drill, an ultrasonic device, a laproscopic instrument, a laser, a cannula, an insufflator, a trocar, scissors, forceps, tubing or a needle. For example, the at least one sealable access site 290 may be configured for insertion of a specific medical instrument. For example, the at least one sealable access site 290 may be configured for insertion of a plurality of medical instruments of a similar size and shape. The at least one sealable access site 290 may be configured to maintain closure of the access site until insertion of one or more medical instruments into the access site 290.

FIG. 3 depicts additional aspects of an apparatus 120. In FIG. 3, a structure 230 of an apparatus 120 is illustrated in cross-section. Correspondingly, the region of the body 110 is similarly illustrated as a partial section of the total region of the body 110. As illustrated in FIG. 3, the structure 230 encloses the isolation field 125. At the face of the structure 230 that is configured to be placed adjacent to the region of the body 110, the engagement surface 225 includes an aperture 210 and a reversible sealing region 220. A gas port 250 is operably connected to a gas duct 235, which is operably connected to a plurality of gas inlets 240. As illustrated in FIG. 3, the apparatus 120 may include a plurality of gas inlets 240 positioned in a grouping on the structure 230. As illustrated in FIG. 3, the apparatus 120 may include a plurality of gas inlets 240 positioned at intervals on a side of the structure 230. The plurality of gas inlets 240 positioned at intervals may be positioned to direct a non-turbulent flow of gas 245 across the aperture 210. When the apparatus 120 is positioned over the region of the body 110, the non-turbulent flow of gas 245 will, therefore, flow across the aperture 210 and the surface of the region of the body 110 exposed through the aperture 210. The structure 230 may be configured so that the non-turbulent flow of gas 245 will be redirected by the side of the structure 230 distal to the plurality of gas inlets 240 to substantially flow (depicted with indicator 310) away from the side of the structure 230 including the engagement surface 225. For example, the side of the structure 230 distal to the plurality of gas inlets 240 may be fabricated to include a curve or angle configured to direct the non-turbulent flow of gas 245 away from the side of the structure 230 including the engagement surface 225. A gas outlet 280, including a filter, is configured to release gas (e.g. indicated as 285), from the isolated field 125 while maintaining positive pressure in the isolation field 125 relative to the outside environment of the structure 230.

FIG. 3 also depicts a sealable access site 290. The sealable access site 290 is configured to allow one or more human fingers or medical instruments access to the medical site 105 while substantially limiting entry of contaminants into the isolation field. The sealable access site 290 is configured to allow one or more human fingers or medical instruments access to the medical site 105 while substantially maintaining positive pressure within the interior of the structure 230. While the sealable access site 290 is described herein as remaining "closed" until a human finger or instrument is inserted, a variety of other approaches may be appropriate in some embodiments. For example, the sealable access site 290 may include an expandable aperture formed by overlapping material with a central passageway, where the aperture expands to accommodate passage of a human finger or instrument. See, for example, U.S. Pat. No. 5,832,925 to Rothrum, titled "Surgical Drape Having Improved Sealing Apparatus," which is herein incorporated by reference. See, for example, U.S. Pat. No. 5,640,977 to Leahy et al., titled "Apparatus and Method for Use in Surgery," which is herein incorporated by reference. See, for example, U.S. Pat. No. 5,480,410 to Cuschieri and Heaven, titled "Extracorporeal Pneumoperitoneum Access Bubble," which is herein incorporated by reference. See, for example, US Patent Application No. 2009/0302545 to Haynes, titled "Peripheral Sealing Gland for Elongate Objects Passing through a Surface or Beyond a Pipe End.," which is herein incorporated by reference. Alternatively, the sealable access site 290 may be of a material, such as latex or silicone, flexible enough to seal around a human finger or instrument during insertion. For example, the sealable access site 290 may have a removable cover.

In the embodiment depicted in FIG. 3, the sealable access site 290 includes a structural region 320 and an access region 325. For example, the structural region 320 may be fabricated from a material of sufficient strength and durability to support a flexible material within the access region 325. For example, the structural region 320 may be fabricated from a durable plastic material. The access region 325 may be fabricated from a material that may be cut to obtain access to the interior of the structure 230. For example, the access region 325 may be fabricated from a thin film of plastic, silicone rubber, or latex rubber. Although not depicted in FIG. 3, the apparatus 120 may also include a removable cover configured to reversibly mate with the sealable access site 290. A removable cover may be fabricated from a material with sufficient strength and hardness to provide structural protection from accidental piercing or breakage of the access region 325, for example during transport or storage. For example, the removable cover may be fabricated from a durable plastic material. A removable cover may include at least one surface configured to reversibly mate with an external surface of the sealable access site 290 in a manner sufficient to substantially impede gas from escaping the interior of the structure 230 through the sealable access site 290 even in situations wherein the sealable access site 290 includes a tear, piercing or break. A removable cover may include an adhesive on the surface positioned to be adjacent to the structural region 320, and therefore provide a barrier sufficient to substantially impede gas from escaping the interior of the structure 230 through the sealable access site 290. A removable cover may include an interfacing surface positioned to be adjacent to the structural region 320, wherein the interface between the surface of the cover and the surface of the sealable access site 290 creates a barrier sufficient to substantially impede gas from escaping the interior of the structure 230 through the sealable access site 290.

FIG. 4 depicts further aspects of an apparatus 120. As illustrated in FIG. 4, an apparatus 120 with a structure 230 includes an engagement surface 225. As illustrated in FIG. 4, the engagement surface 225 may include a reversible sealing region 220, wherein the reversible sealing region 220 is positioned to come into contact with the region of the body 110 when the apparatus 120 is placed on the region of the body 110. As illustrated in FIG. 4, the engagement surface 225 may include a film 400. As illustrated in FIG. 4, the engagement surface 225 may include a film 400, wherein an aperture in the engagement surface 225 substantially includes the film 400. The film 400 may be discontinuous with the aperture in the engagement surface 225, for example the film 400 may include an aperture. The film 400 may be configured as a means of providing a seal with the region of the individual body 110. For example, see U.S. Pat. No. 4,275,719 to Mayer, titled "Apparatus and Method for Providing an Aseptic Surgical Environment," which is herein incorporated by reference. The film 400 may be of a variety of materials, and may include at least one of: polyvinylidene fluoride, polyethylene, polyvinyledene, polyolefin, polyester, cellulose acetate, polyamide or ethylene vinyl acetate. The film 400 may be a porous film. The film 400 may be a breathable film. During use, the film 400 may be pierced or cut, such as with a medical instrument, to create an aperture in the film 400. The film 400 may be an incise film. The film 400 may be configured in layers. The engagement surface 225 may include the film 400 over a substantial portion of the surface of the engagement surface 225, or the film may comprise a region of the engagement surface 225. The film 400 may include a surface configured to be placed in contact with the surface of the medical site at the region of the body 110. The film 400 may include a surface configured to be placed in contact with the medical site 105. The film 400 may be configured to be penetrated to allow access to the medical site. The film may be positioned to provide access for incising the lesion or surgical site. For example, the film 400 may be fabricated from a thin film that may be punctured, cut, or torn with a medical instrument inserted through the access site 290. The film 400 may include at least one adhesive. The film 400 may include an adhesive on at least one surface of the film 400. The film 400 may include an adhesive on the surface of the film 400 configured to be positioned adjacent to the surface of the region of the body 110. Suitable adhesives include those described herein as suitable for use in relation to the reversible sealing region 220.

A film 400 may include at least one of a medicinal, microcidal or microstatic compound. For example, the film may include those described in U.S. Pat. Nos. 5,979,450 and 6,742,522 to Baker et al., both titled "Surgical Incise Drape," and both herein incorporated by reference. For example, the film may include an incise film. For example, the film may include the Ioban™ Incise Film manufactured by 3M Corporation, with corporate headquarters in St, Paul, Minn. The product brochure titled "3M™ Steri-Drape™ Cardiovascular Sheets with Ioban™ 2 Incise Film" bearing a company identifier of 70-2008-5487-8(1081)ii is herein incorporated by reference. The product brochure titled "3M™ Steri-Drape™ Cardio/Chest Drape with Ioban™ 2 Incise Film-6682" bearing a company identifier of 70-2009-8629-0 is herein incorporated by reference. For example, a film 400 may include at least one of a medicinal, microcidal or microstatic compound on the surface of the film positioned to be adjacent to the medical site on the region of the body when the apparatus 120 is positioned relative to the region of the body 110. For example, the surface of the film 400 may include at least one antibiotic, iodophore, silver-containing compound, or alcohol-containing compound. For example, the surface of the film 400 may include gentamicin, tetracycline, erythromycin, bactracin zinc, or other antibiotic-containing compound. The film 400 may include at least one silver-containing compound, for example silver nitrate or silver sulfadiazine (e.g. Thermazene™, Silvadene™ and Flamazine®). The film 400 may include a knitted polyester film such as Acticoat™, available from Smith and Nephew Corporation, London England. The film 400 may include a fine fabric such as Actisorb Silver™, available from Ethicon Inc, Somerville N.J. The film 400 may include a silver compound. The film 400 may include a porous element such as Silverlon® NPD, available from Argentum Medical, LLC, Geneva Ill. See also Silver et al., "Silver as Biocides in Burn and Wound Dressings and Bacterial Resistance to Silver Compounds," *Journal of Industrial Microbiology and Biotechnology*, vol. 33, pages 627-634, (2006), which is herein incorporated by reference. See also Gago et al., "A Comparison of Three Silver-containing Dressings in the Treatment of Infected, Chronic Wounds," *Wounds*, Vol. 20, No. 10, pages 273-278 (2008), which is herein incorporated by reference. The film 400 may include an antibiotic, and the film 400 may be fabricated with the antibiotic in a controllable-release matrix. See, for example, Elsner et al., "Novel Biodegradable Composite Wound Dressings With Controlled Release of Antibiotics: Microstructure, Mechanical and Physical Properties," *Journal of Biomedical Materials Research B: Applied Biomaterials*, Vol. 93B, pages 425-435 (2010), which is herein incorporated by reference. The film 400 may include an antibacterial nanomedicine such as those described in Yacoby and Benhar, "Antibacterial Nanomedicine," *Nanomedicine*, Vol. 3, No. 3, pages 329-341, (2008), which is herein incorporated by reference. The film 400 may include shell crosslinked nanoparticles including silver antimicrobials such as described in Li et al., "Shell Crosslinked Nanoparticles Carrying Silver Antimicrobials as Therapeutics," Chemical Communications, Vol. 46, Pages 121-123 (2010), which is herein incorporated by reference. The film 400 may include chitosan or collagen. See, for example, U.S. Pat. No. 6,967,261 to Soerens and Malik, titled "Bandage, Methods of Producing and Using Same," which is herein incorporated by reference. See, for example, Brett, "A Review of Collagen and Collagen-Based Wound Dressings," *Wounds* Vol. 20, No. 12 (2008), which is herein incorporated by reference. The film 400 may be inclusive to a wound dressing. The film 400 may be configured to adhere to the surface of the region of the body 110 after removal of the apparatus 120, for example the film may include a circumference region configured to be disassociated from the apparatus 120. The film 400 may include a compound configured for the release of nitric oxide. See, for example, U.S. Pat. No. 5,519, 020 to Smith et al, titled "Polymeric Wound Healing Accelerators," which is herein incorporated by reference. See, for example, US Patent Application No. 2009/0131883 to Av-Gay and Greenberg, titled "Antimicrobial Gas-Releasing Ear Drainage Tubes," which is herein incorporated by reference. See, for example, U.S. Pat. No. 5,519,020 to Smith et al., titled "Polymeric Wound Healing Accelerators," which is herein incorporated by reference.

FIG. 4 depicts aspects of an embodiment of the apparatus 120. As illustrated in FIG. 4, an apparatus 120 may include a gas port 250 operably connected to a gas supply duct 235 and a gas inlet 240 configured to supply a non-turbulent flow of gas 245 traversing a surface of an individual body. An apparatus 120 includes a gas port 250, which, as depicted in FIG. 4, may be operably connected to a gas supply duct 235 and a gas inlet 240 configured to supply a non-turbulent flow of gas 245 substantially in parallel with a region of the surface of an individual body 110. As illustrated in FIG. 4, a gas inlet 240 may be oriented and positioned so that the non-turbulent flow of gas 245 traverses the surface of the individual body wherein the engagement surface 225 includes a reversible sealing region 220 and a film 400. Some embodiments may include at least one cover 440, wherein the at least one cover 440 is configured to reversibly attach to the engagement surface 225. The at least one cover 440 may be single-use and disposable. For example, the at least one cover 440 may be fabricated from a sheet fabricated from paper or plastic, and be configured of a shape and form to reversibly attach to the engagement surface 225 prior to placement of the apparatus 120 adjacent to the region of the body 110. To prepare the apparatus 120 for use, a cover 440 may be removed to expose the engagement surface 225 for placement adjacent to the region of the body 110. The structure 230 also includes one or more gas outlet 280, 460, wherein the one or more gas outlet 280, 460 is distally positioned on the structure 230 from the gas inlet 240, and wherein the one or more gas outlet 280, 460 is configured to release a gas from the isolated field 125 while maintaining positive pressure in the isolation field 125 relative to the outside environment of the structure 230. The one or more gas outlet 280, 460 may include a filter. The apparatus 120 also includes a sealable access site 290. The sealable access site 290 may include a structural region 320 and an access region 325.

The apparatus 120 may include at least one cover 430, wherein the cover 430 is configured to reversibly attach to the surface of the at least one sealable access site 290. The at least one cover 430 may be single-use and disposable. The at least one cover 430 may be durable and configured for multiple use. For example, the at least one cover 430 may be fabricated from a sheet of paper or plastic, and be configured of a shape and form to reversibly attach to the at least one sealable access site 290. The cover may include multiple adhesive layers configured in parallel, and be configured so that individual layers may be removed during use to provide a fresh surface of the cover for use. When access is desired through the sealable access site 290, the cover 430 may be removed. In some embodiments, the cover 430 may be configured to be reusable.

As illustrated in FIG. 4, the apparatus 120 may include an opposing face 450 of the structure 230, wherein the opposing face 450 is opposite to the engagement surface 225. The opposing face 450 may include the at least one sealable access site 290. The at least one sealable access site 290 may be positioned at a side of the structure 230 opposite to the one or more gas inlets 240. The at least one sealable access site 290 may be positioned at a side of the structure 230 distal to the gas port 250. The opposing face 450 may include one or more gas outlet 460, wherein the one or more gas outlet 460 includes at least one filter configured to substantially sterilize the gas released from the isolation field 125. The opposing face 450 may include at least one cover 430 configured to reversibly attach to an exterior of the opposing face 450 of the structure 230. For example, the at least one cover 430 may be fabricated from a sheet of paper or plastic, and be of a shape and form to reversibly attach to an exterior of the opposing face 450 of the structure 230.

Further aspects of an apparatus 120 are depicted in FIGS. 5A and 5B. As illustrated in FIG. 5A, in some embodiments an apparatus may take a condensed, collapsed or compact form. For example, the smaller condensed form of the apparatus, illustrated in FIG. 5A, may be configured for storage or transport. The apparatus 120 may be enlarged or expanded as needed for use, as depicted in FIG. 5B. FIG. 5B depicts the apparatus 120 illustrated in FIG. 5A with the structure 230 fully expanded. In some embodiments, the apparatus 120 may include a structure 230 including a flexible material. In some embodiments, the apparatus 120 may include a structure 230 including a flexible material, wherein the flexible material is configured to allow the apparatus 120 to be stored in a condensed or compact form. For example, the flexible material may include ethylene vinyl acetate. In some embodiments, the apparatus 120 may include a structure 230 including a flexible material, and a frame configured to support the flexible material. Structural supports may also be included. See, for example, U.S. Pat. No. 5,316,541 to Fischer, titled "Enclosure for Surgical Procedures," which is herein incorporated by reference. The structure 230 may include a plurality of ring-like units 500 flexibly interconnected and configured to provide radial support. The ring-like units may be flexible, or they may be inflexible and substantially rigid. For example, as depicted in FIGS. 5A and 5B, a frame configured to support the flexible material may include ring-like units 500. The ring-like units 500 may be oriented in a linear alignment along the expandable dimension of the structure 230. There may be regions of flexible material between the ring-like units 500 of the structure 230. The apparatus 120 may be configured to allow the regions of flexible material between the ring-like units 500 to bend, fold or compress while the apparatus 120 is in a condensed or compact form (e.g. FIG. 5A). The structure 230 may include a plurality of ring-like units 500 of a plurality of sizes which are configured to fit into each other to collapse the structure 230 and telescope up to expand the structure 230. The structure 230 of the apparatus 120 may be formed by a plurality of rings of a plurality of sizes which fit into each other to collapse the structure 230 and telescope up to expand the structure 230. The apparatus 120 may include supports external to the structure 230. The apparatus 120 may include joints configured to bend or lock into place during expansion or compression of the structure 230. The apparatus 120 may include joints, and the joints may be configured to reversibly lock into position. For example, the apparatus 120 may include joints configured to reversibly lock into position along the outer edge of the structure 230. During use in some embodiments, the net gas flow 245 into the structure 230 may inflate or expand the structure 230 due to positive pressure within the structure 230 relative to the region external to the structure 230. See, for example, U.S. Pat. No. 5,020,546 to Russo, titled "Casualty Wrap with Integral Medical Access Chamber," which is herein incorporated by reference. In some embodiments, the apparatus 120 may be configured to allow a user to expand the structure manually before use. Once the structure 230 has expanded (e.g. FIG. 5B), a positive pressure within the structure 230 relative to the region external to the structure 230 may be maintained through manual control or electronic control.

Figure 6:
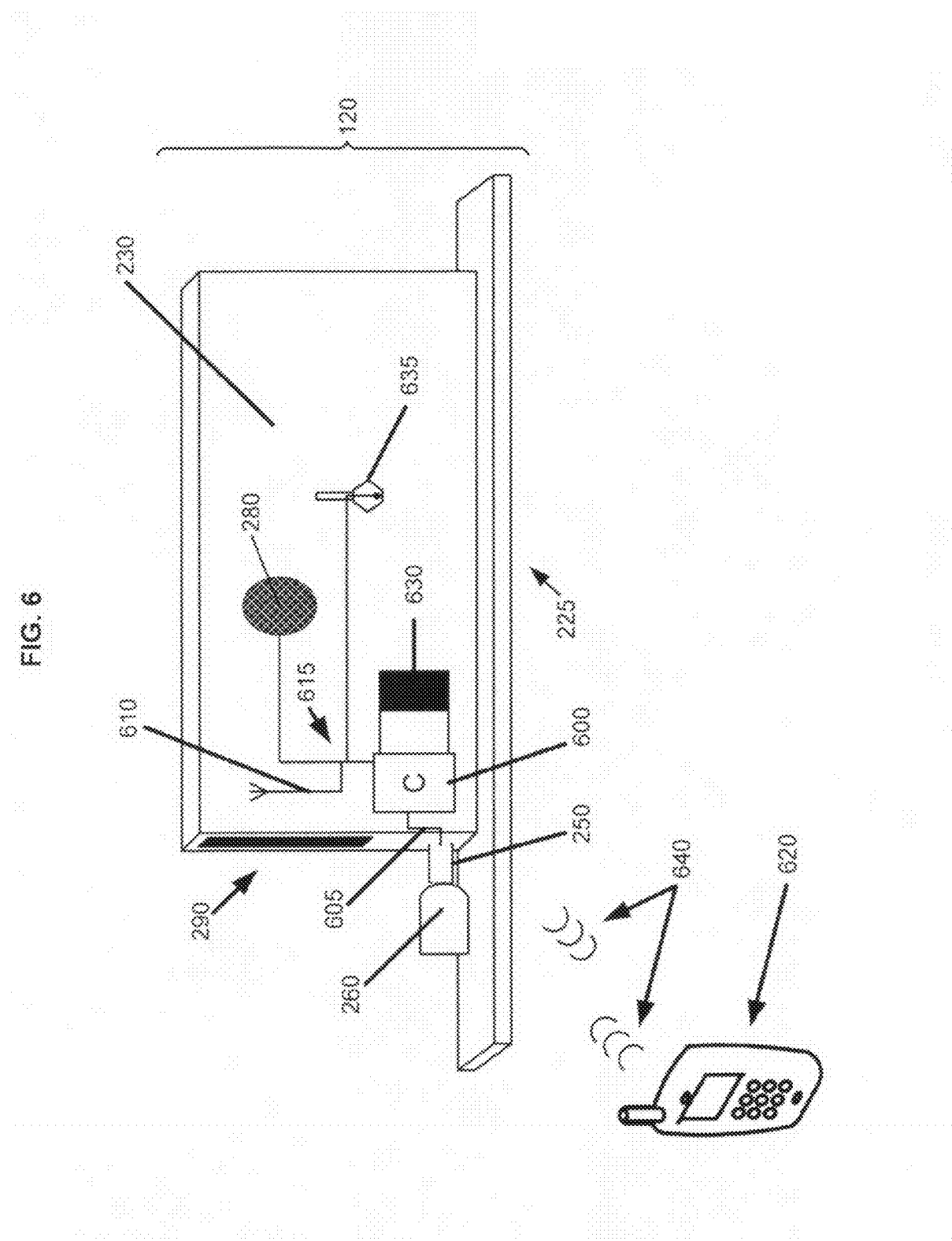
FIG. 6 is a schematic of an apparatus.

FIG. 6 depicts aspects of the apparatus 120 described herein. FIG. 6 illustrates an apparatus 120 including a structure 230. FIG. 6 depicts the structure 230 as a rectangular structure, a configuration that may be desirable for embodiments configured for use along the long axis of a limb (e.g. an arm or leg). The apparatus 120 depicted in FIG. 6 includes an engagement surface 225 which has a larger cross-section than the structure 230. This additional area may be configured, for example, to provide stability to the structure 230 when it is in use. In some aspects, the additional area may be configured as a restraining unit configured to stabilize the position of the engagement surface 225 relative to a region of an individual body. The apparatus 120 illustrated in FIG. 6 shows that one or more of the at least one sealable access site 290 may be positioned on a side of the structure 230, wherein the side of the structure 230 is adjacent to the engagement surface 225. The apparatus 120 depicted in FIG. 6 includes a gas port 250 operably connected to a gas source 260. The gas source 260 depicted in FIG. 6 is illustrated as a tank of stored gas positioned along the axis of the apparatus 120 parallel with the engagement surface 225. Such an alignment may provide additional stability to the apparatus relative to a region of an individual body. The apparatus 120 includes a sealable access site 290.

Figure 7:
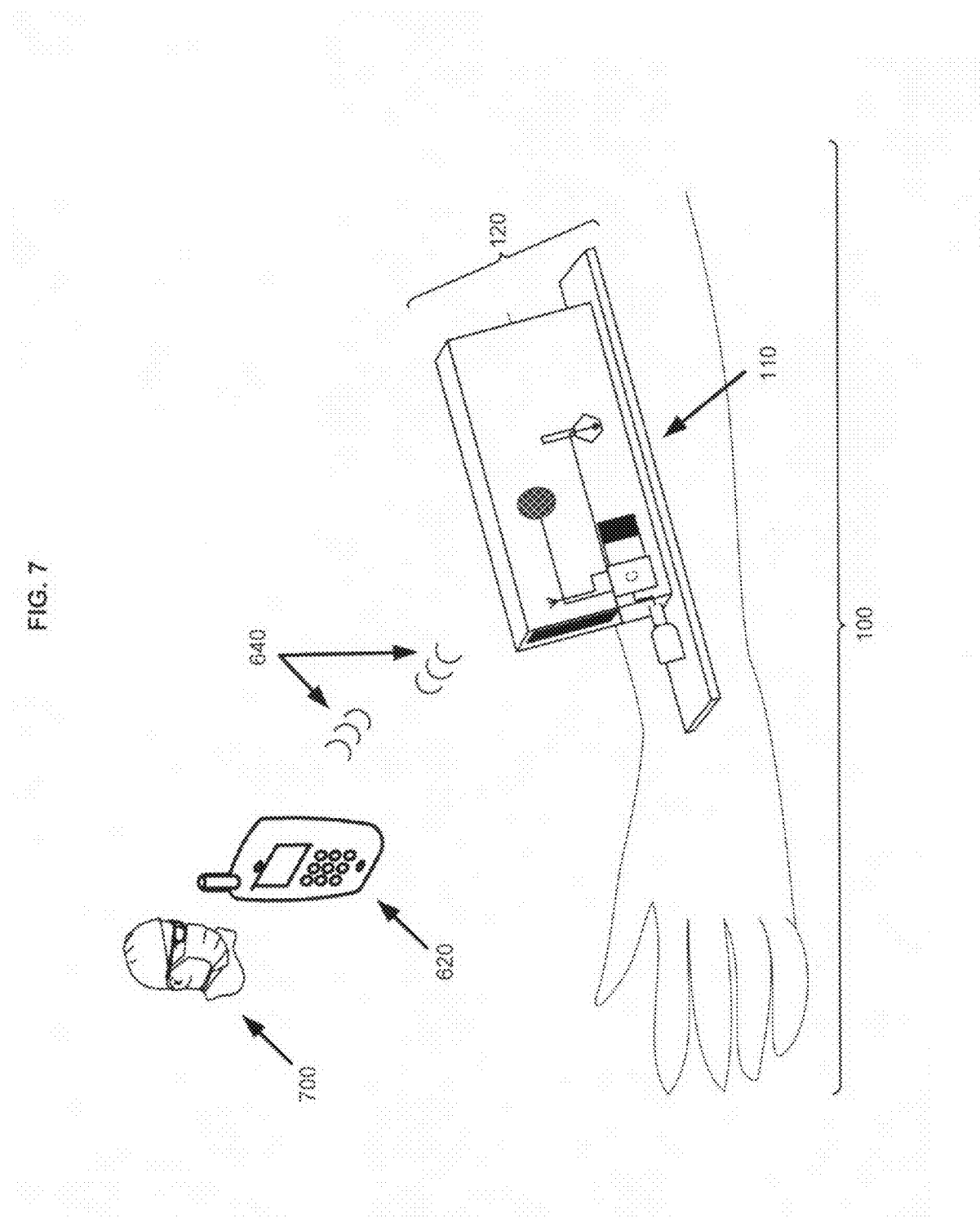
FIG. 7 is a schematic of the apparatus as depicted in FIG. 6 during implementation.

The apparatus 120 illustrated in FIG. 6 includes an electronic controller 600 (also marked with the letter "C") operably connected to both the gas port 250 and to the gas outlet 280. Although the electronic controller 600 is illustrated as operably connected by wires 605, 615 in FIG. 6, in some embodiments the electronic controller 600 may be operably connected to other components of the apparatus 120 with wireless connections. An electronic controller 600 which is operably connected to both the gas port 250 and the gas outlet 280 may serve to maintain the positive pressure within the structure 230 by controlling the relative rate of gas flow through the gas port 250 and the gas outlet 280. For example, the electronic controller 600 illustrated in FIG. 6 is connected to the gas port 250 by a wire 605. For example, the electronic controller 600 may be operably connected to a valve controlling the rate of gas flow through the gas port 250. For example, the electronic controller 600 may be operably connected to a valve controlling the rate of gas flow through a gas inlet (not illustrated in FIG. 6). For example, the electronic controller 600 may be operably connected to a valve controlling the relative proportions of gas flow from different gas sources to a gas inlet. Control by the controller of the relative proportions of gas flow from different gas sources to a gas inlet control may be variable. For example, the controller may include a preprogrammed series wherein the gas flow originates from different gas sources over time. For example, the controller may include a preprogrammed series wherein the gas flow is initially from a first source for a set period of time, then from a second source for a set period of time and then from a third source for the duration of use. For example, the controller may include a conditional set of parameters such as in response to a manual control unit (e.g. a switch, dial or other manual control unit) to change the gas source in use, or relative rates from multiple gas sources in use. For example, the controller may include a conditional set of parameters such as a response to a situational parameter (e.g. if the temperature of the unit is above 85 degrees, nitrogen gas should substantially be included in the gas flow). Similarly, for example, the electronic controller 600 may be operably connected to a valve controlling the rate of gas flow through the gas outlet 280. For example, the electronic controller 600 illustrated in FIG. 6 is connected to the gas outlet 280 by a wire 615. For example, the electronic controller 600 may be operably connected to a unit controlling the rate of gas flow through the gas outlet 280. The rate of gas flow through the gas outlet 280 may be variable over time, and may be increased or decreased responsive to signals from the electronic controller 600. For example, an electronic controller 600 may be programmed to signal for a high gas flow rate for a set period of time, followed by a lower gas flow rate for a set period of time. The electronic controller 600 may be operably connected to a power source 630. As illustrated in FIG. 6, an electronic controller 600 may be directly attached to a power source 630. For example, a power source may include a battery, a solar cell, or a wire connection to an external supply of power (e.g. a wall power socket). The electronic controller 600 may be operably connected to one or more sensors, such as a temperature sensor 635, or pressure sensor. The electronic controller 600 may be configured to be responsive to one or more sensors. For example, the electronic controller 600 may be configured to create a signal initiating a higher gas flow in response to a sensor result indicating decreased pressure within the apparatus 120. The electronic controller 600 may be operably connected to an antenna 610, which may be configured to transmit and receive signals 640 from an external device 620. As illustrated in FIGS. 6 and 7, an apparatus 120 may include electrical circuitry. An apparatus 120 may include an electro-mechanical system.

An external device 620 may include a computing device such as a laptop or desktop computer, or a networked computer system. For example, the external device 620 may include a computing device that is part of a medical facility computing system, or an emergency-response computing system. An external device 620 may include a handheld electronic device such as a cell phone, personal data assistant (PDA) or other handheld electronic device. For example, the external device 620 may include a handheld device configured for use by an individual person. For example, the external device 620 may include a handheld device configured for use by a medical professional or an emergency-response professional. An electronic controller 600 may be configured to send a signal 640 to an external device 620 in response to a condition, such as the onset of gas flow, manual operation of the apparatus 120, or reduced gas flow rate from one or more gas source. An external device 620 may be configured to send a signal 640 to the apparatus 120 for transmission to an electronic controller 600. For example, an external device 620 may be configured to send a signal 640 to the apparatus 120 for transmission to an electronic controller 600, wherein the electronic controller 600 is configured to respond to the signal 640 with the initiation of a series. For example, an external device 620 may be configured to send a signal 640 to the apparatus 120 for transmission to an electronic controller 600, wherein electronic controller 600 is configured to respond to the signal 640 from the external device 620 with a responsive signal 640 from the electronic controller 600.

The apparatus 120 illustrated in FIG. 6 may also include one or more electronic data storage devices. The one or more electronic data storage devices may be configured to store information relating to the operation of the apparatus 120, for example to store information relating to the rate of gas flow through the gas port 250. The one or more electronic data storage devices may be configured to store information relating to the operation of the apparatus 120, for example to store information relating to the rate of gas flow through the gas outlet 280. The one or more electronic data storage devices may be configured to store information relating to the operation of the apparatus 120, for example to store information relating to one or more sensors, such as the temperature reading of a temperature sensor 635, or the ambient atmospheric pressure external to the apparatus 120. The one or more electronic data storage devices may be configured to store information relating to the operation of the apparatus 120 at a set time point or at a series of time points. The one or more electronic data storage devices may be configured to store information relating to signals 640 transmitted and received by the antenna 610, for example the time, duration or information content of the signals. The one or more electronic data storage devices may be configured to store other information, such as time or positioning information (e.g. global positioning system ("GPS") information). The one or more electronic data storage devices may be part of a data processing system.

FIG. 7 illustrates potential use of an apparatus 120 such as that illustrated in FIG. 6. An apparatus 120 may be positioned relative to a region 110 of an individual person's body, which in FIG. 7 includes the forearm and wrist of an individual person 100. Signals 640 may be transmitted from the apparatus 120 and to the apparatus 120 from an external device 620. A user 700 may operate the external device 620 to visualize information from the apparatus 120. For example, the external device 620 may include a display screen to display information relating to the operation of the apparatus 120. For example, the external device 620 may include a display screen to display information transmitted from the apparatus 120. A user 700 may operate the external device 620 to transmit information, which may include instructions, to the apparatus 120. For example, the external device 620 may include a keypad which may be manipulated by a user 700 to transmit information to an apparatus 120. A user 700 may include medical personnel, such as a doctor, nurse, or emergency medical technician (EMT). A user 700 may include individuals interested in monitoring the use of the apparatus 120, such as relatives, insurance providers, and emergency-response personnel. Although user 700 is depicted herein as a single illustrated figure, user 700 may be representative of a human user, a robotic user (e.g., computational entity), and/or substantially any combination thereof (e.g., a user may be assisted by one or more robotic agents) unless context dictates otherwise. In general, the same may be said of "sender" and/or other entity-oriented terms as such terms are used herein unless context dictates otherwise.

Figure 8:
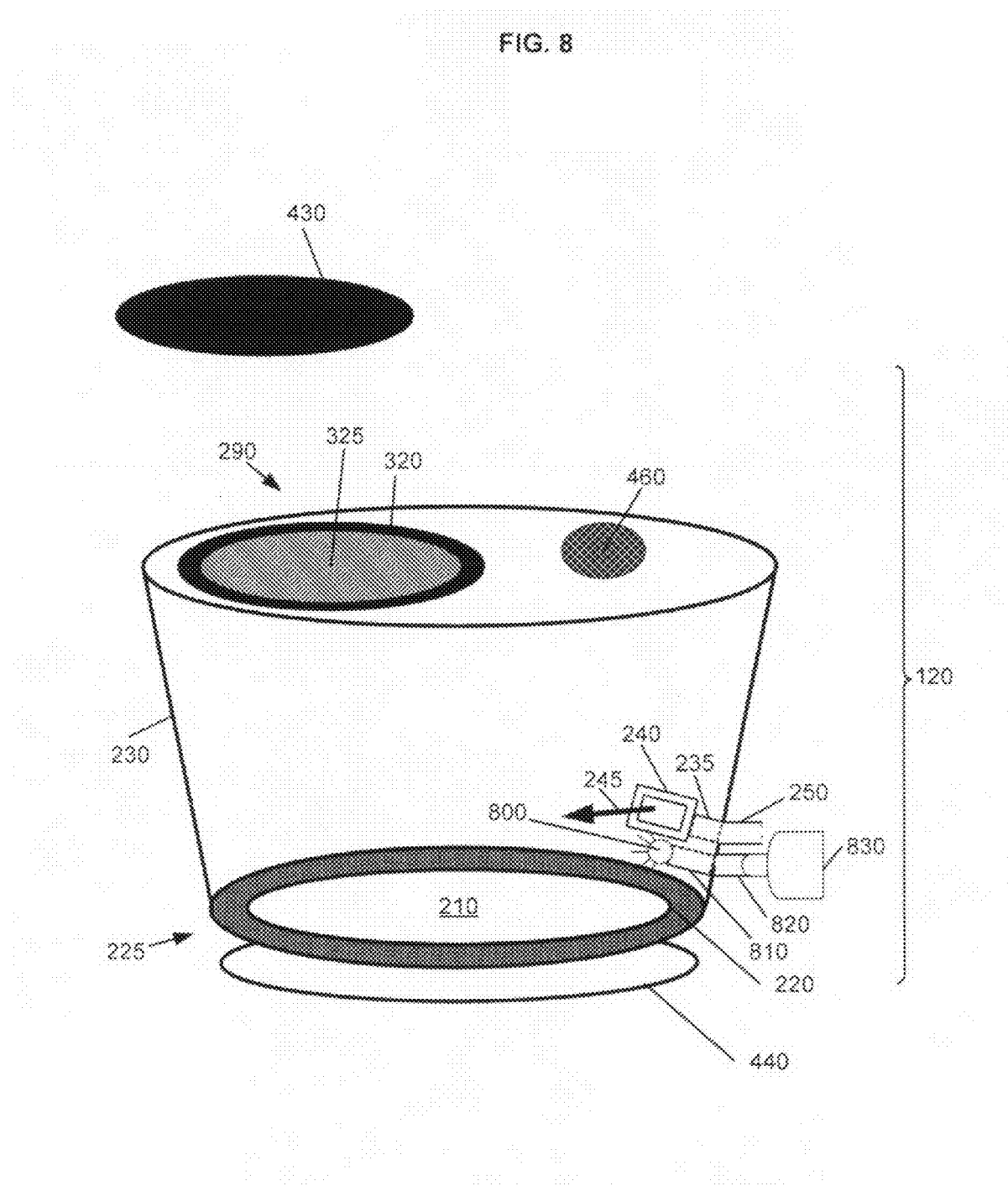
FIG. 8 is a schematic of an apparatus.

FIG. 8 depicts aspects of an embodiment of an apparatus 120. As illustrated in FIG. 8, an apparatus 120 includes a structure 230. The structure 230 includes an engagement surface 225. The engagement surface 225 includes a reversible sealing region 220. The engagement surface 225 includes an aperture 210. Although the aperture 210 is illustrated as centered within the engagement surface 225 and encompassing the central region of the engagement surface 225, in some embodiments the aperture 210 may be non-symmetrically placed relative to the engagement surface 225. The aperture 210 may be of various sizes relative to the engagement surface 225, depending on the embodiment. The apparatus 120 includes a cover 440, which is configured to reversibly attach to the engagement surface 225. The cover 440 may be configured with a plurality of layers, wherein individual layers may be removed in series to expose a fresh surface of the cover for subsequent use. The cover 400 may be configured to substantially seal the engagement surface 225 and aperture 210 after use of the apparatus 120, for example for disposal. In some embodiments, the cover 440 is of a size and shape to cover the entirety of the engagement surface 225. In some embodiments, the cover 440 is of a size and shape to cover the entirety of the aperture 210. The structure 230 includes a sealable access site 290. The sealable access site 290 includes a sealable access region 325, and a structural region 320. The structure 230 includes a gas outlet 460. The apparatus includes a sealable access site cover 430. In some embodiments, the sealable access site cover 430 may be of a size and shape to cover the entirety of the sealable access region 325. In some embodiments, the sealable access site cover 430 may be of a size and shape to cover the entirety of the sealable access region 325 and the structural region 320.

FIG. 8 depicts that the apparatus 210 includes a gas port 250, a gas supply duct 235 and a gas inlet 240. The gas inlet 240 is oriented to maintain a non-turbulent flow of gas 245 traversing at least a part of the surface of a region of an individual body while the apparatus 120 is in use. For example, the gas inlet 240 is oriented to maintain a non-turbulent flow of gas 245 traversing the surface of a region of an individual body exposed through the aperture 210 while the apparatus 120 is in use. Also depicted in FIG. 8 is a device 800 operably attached to the structure 230 of the apparatus 120. The device 800 is configured to dispense one or more compounds into the interior of the structure 230. For example, the device 800 may be configured to direct aerosol in the direction of the aperture 210 at the engagement surface 225. The device 800 may include a spray nozzle, a plurality of spray nozzles, an atomizer, a vaporizer, or other devices as appropriate to the embodiment. As depicted in FIG. 8, the device 800 is operably attached to a conduit 810, which is configured as a channel for fluid to the device 800. FIG. 8 depicts a port 820 operably attached to the conduit 810, wherein the port 820 is configured to couple a reservoir 830 access region with the conduit 810. The reservoir 830 may include one or more compounds in a formulation suitable for dispensing into the interior of the structure. For example, the reservoir may include compounds in a fluid form, wherein the one or more compounds are in a formulation that is anticipated to be stable in aerosolized form. A reservoir 830 may be configured to be refillable or rechargeable. Depending on the embodiment, the types and formulations of the compounds may vary. Examples of compounds that are suitable for use in various embodiments are described above.

Figure 9:
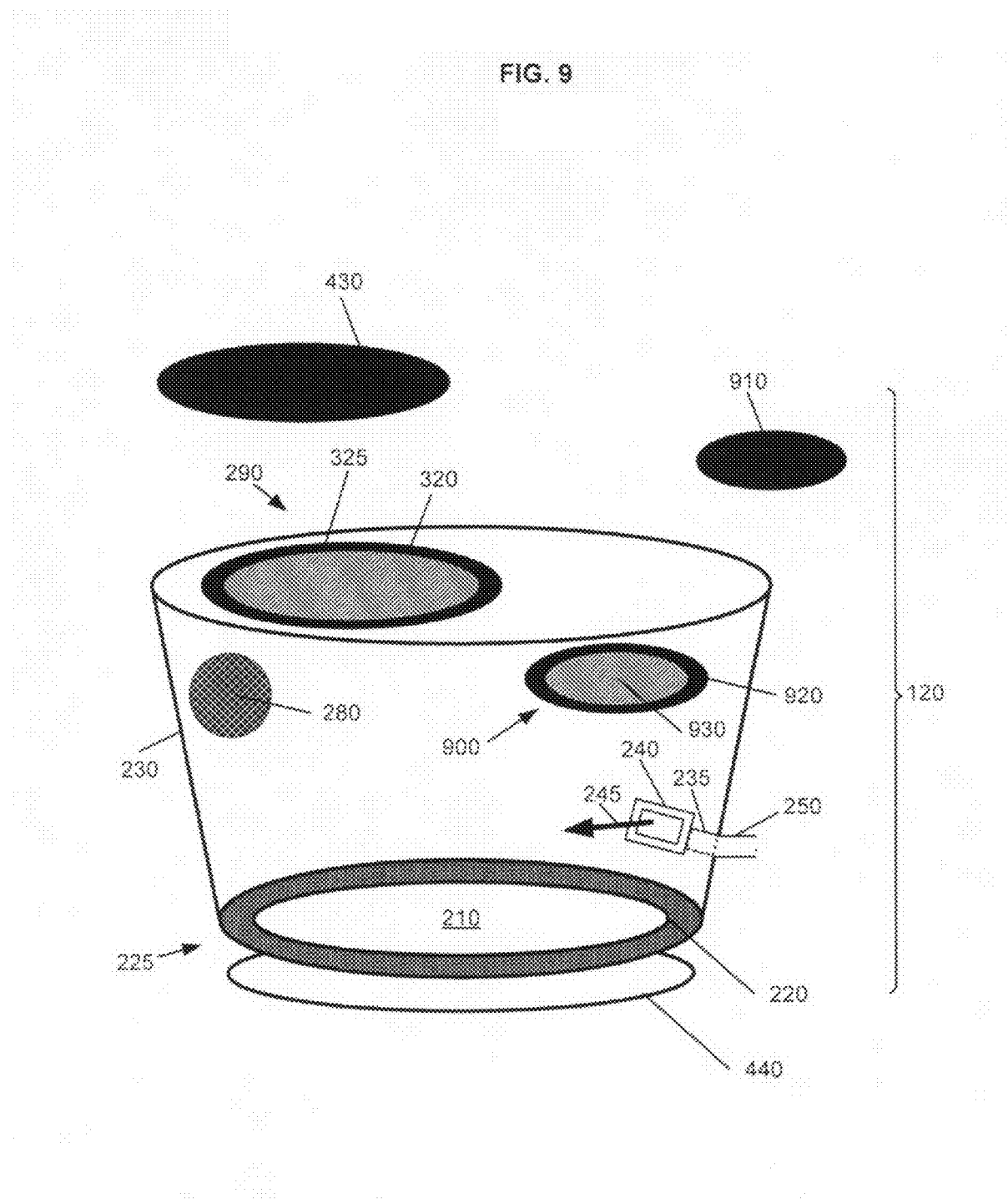
FIG. 9 is a schematic of an apparatus.

FIG. 9 depicts an embodiment of an apparatus 120. As depicted in FIG. 9, an apparatus 120 includes an engagement surface 225. The engagement surface 225 includes an aperture 210 and a reversible sealing region 220. A cover 440 is configured in a size and shape to mate with the entire engagement surface 225. The apparatus 120 depicted in FIG. 9 includes a gas port 250, a gas supply duct 235, and a gas inlet 240. The gas inlet 240 depicted in FIG. 9 is oriented to direct the gas flow 245 from the gas inlet 240 into the interior of the structure 230. The structure 230 includes a gas outlet 280. The structure 230 includes a sealable access site 900 on a side of the structure 230 adjacent to the engagement surface 225. The sealable access site 900 depicted in FIG. 9 includes an access region 930 and an associated structural region 920. A cover 910 is configured to reversibly mate with the exterior surface of the sealable access site 900. The structure 230 includes another sealable access site 290, located on a side of the structure 230 opposite to the engagement surface 225. The sealable access site 290, located on a side of the structure 230 opposite to the engagement surface 225, includes a structural region 320 and an access region 325. A cover 430 is configured to reversibly mate with the exterior surface of the access region 325 of the sealable access site 290. As illustrated in FIG. 9, in some embodiments there may be a plurality of access sites 900, 290, which may be configured in different sizes and shapes. As illustrated in FIG. 9, in some embodiments there may be a plurality of access sites, 900, 290, which may be configured on varying faces of the structure 230. As illustrated in FIG. 9, in some embodiments there may be a plurality of access sites, 900, 290, which may be configured for insertion of varying medical instruments and/or human fingers into the interior of the structure 230.

In various embodiments, the apparatus 120, including all ports and outlets, may be of a size and weight, as well as durability, suitable for carrying in a field or combat situation. The apparatus 120 may be of a size, weight and ruggedness for carrying in an emergency-readiness package. The apparatus 120 may be of a size, weight and ruggedness for storage in a vehicle, for example for emergency use. The apparatus 120 may be of a size, weight and ruggedness for carrying on an individual person. For example, the apparatus 120 may be of a size, weight and ruggedness suitable for carrying within a backpack, in a satchel or in a field kit. For example, the apparatus 120 may be of a size, weight and ruggedness suitable for carrying within a medical kit configured for carrying by an individual person. For example, the apparatus 120 may be of a size, weight and ruggedness suitable for carrying within an emergency kit configured for carrying by an individual person. The apparatus 120, including all ports and outlets, may be sterilized and packaged in a sterile form in a sterile container for storage until use. The apparatus 120 may include sterile packaging for all or part of the apparatus. See, for example, U.S. Pat. No. 5,174,306 to Marshall, titled "Method and Apparatus for Forming a Sterile Field," which is herein incorporated by reference.

Methods for the use of the apparatuses described herein include methods for establishing and maintaining an isolation field adjacent to the surface of a region of an individual body. Methods for the use of the apparatuses described herein include methods for establishing an isolation field around a medical site. Methods include: sealably coupling an apparatus over a medical site to define an isolation field; maintaining a non-turbulent flow of gas within the apparatus; and outletting gas from the apparatus through one or more gas outlets while maintaining positive pressure within the isolation field. Methods described herein include a method for maintaining an isolation field around a medical site, including maintaining positive pressure within the isolation field.

Methods include sealably coupling an apparatus to the surface of a region of an individual body over a medical site. The coupling is of a type configured to be reversible with minimal discomfort to an individual on whose body a medical site lies. For example, the coupling may be achieved with medical or surgical grade adhesives. For example, the coupling may be achieved with a film. For example, the coupling may be achieved with an incise film. For example, the coupling may be achieved with moderate suction to the surface of region of the individual body surrounding the medical site. For example, the coupling may be stabilized with a restraining unit, such as a strap, bandage, tape, tie or band. In some embodiments, sealably coupling an apparatus over a medical site includes sealing an adhesive film over the surface of a medical site. In some embodiments, sealably coupling an apparatus over a medical site includes removing a cover from the apparatus, and sealing an adhesive film over the surface of a medical site. For example, the apparatus may include a disposable cover over the engagement surface during storage, which is configured for removal before operation of the apparatus. In some embodiments, sealably coupling an apparatus over a medical site includes employing suction to adhere the apparatus to the circumference of the medical site. In some embodiments, sealably coupling an apparatus over a medical site includes sealably coupling the apparatus around the circumference of the medical site. For example, the apparatus may be of a size and shape to reasonably conform to the circumference of medical sites on an individual body part, such as a hand, arm, leg or torso.

Methods include maintaining a non-turbulent flow of gas within the apparatus. For example, the non-turbulent flow of gas may be maintained in a direction to traverse at least a portion of the surface of the medical site. For example, maintaining a non-turbulent flow of gas may include maintaining a non-turbulent flow of gas in a net flow direction across the surface of the medical site. For example, maintaining a non-turbulent flow of gas may include maintaining a non-turbulent flow of gas in a net flow direction substantially parallel to the surface of the medical site. For example, maintaining a non-turbulent flow of gas may include directing the gas from a plurality of gas inlets within the apparatus. For example, maintaining a non-turbulent flow of gas may include adjusting the relative flow rate and direction of the flow of gas relative to the medical site. For example, the flow rate of the gas may be increased, or the flow rate of the gas may be decreased. For example, maintain a non-turbulent flow of the gas may be utilized to substantially maintain the integrity of the isolation field. For example, the direction of the gas flow relative to the medical site may be altered so that the gas flow substantially traverses at least a region of the medical site. For example, the direction of the gas flow relative to the medical site may be modified so that the gas flow substantially traverses at least a part of a surface of the individual body including the medical site. Such modification or alteration of the gas flow direction may be necessary, for example, after the apparatus is coupled over the medical site. Such modification or alteration of the gas flow direction may be desirable, for example, to mitigate discomfort to the individual. Such modification or alteration of the gas flow direction may be desirable, for example, to remove contaminating particles from the medical site. Such modification or alteration of the gas flow direction may be desirable, for example, to decrease the movement of particles originating from the medical site. For example, maintaining a non-turbulent flow of gas may include removing contaminants from the medical site with the non-turbulent flow of gas. For example, maintaining a non-turbulent flow of gas may include isolating a substance originating at the medical site, e.g. to isolate a bloodborne pathogen. A substance may include a nonendogenous substance such as a toxin, poison, or chemical to which the site has been exposed, purposely or nonpurposely. A substance may include a hazardous material, radioactive material, teratogenic material, or carcinogenic material being used in the treatment of the individual, e.g. for as a treatment for cancer. A substance may include a pathogen, e.g. a blood-borne pathogen. For example, maintaining a non-turbulent flow of gas may include maintaining isolation of a field against one or more substance from an environment external to the isolation field. For example, maintaining a non-turbulent flow of gas may include maintaining isolation of the field against one or more pathogen from an environment external to the isolation field. For example, maintaining a non-turbulent flow of gas may include maintaining isolation of the field against one or more synthetic substance from an environment external to the isolation field, e.g. toxin, poison, chemical, hazardous material, radioactive material, teratogenic material, carcinogenic material. For example, maintaining a non-turbulent flow of gas may include maintaining isolation of the field against one or more synthetic substance including a radioactive therapy within a patient following e.g. implantation (brachytherapy), systemic therapy (such as radioimmunotherapy and radiopharmaceutical therapy) or for preoperative labeling, such as of lymph nodes. For example, maintaining a non-turbulent flow of gas may include maintaining isolation of the field against one or more natural substance from an environment external to the isolation field. For example, maintaining a non-turbulent flow of gas may include maintaining isolation of the field against one or more allergen, pollen, dirt, biologic, biochemical, pathogen, virus, bacteria, fungus, or parasite.

Methods include maintaining a non-turbulent flow of gas within the apparatus, while altering the composition of non-turbulent flow. For example, maintaining a non-turbulent flow of gas may include altering the composition of gas included in the non-turbulent flow of gas. Methods include maintaining a non-turbulent flow of gas within the apparatus, wherein the composition of the gas is specific to a medical situation. Methods include maintaining a non-turbulent flow of gas within the apparatus, wherein the composition of the gas is specific to an emergency situation. For example, maintaining a non-turbulent flow of gas may include maintaining a non-turbulent flow of a gas configured for fire suppression. For example, the gas may include a substantial proportion of nitrogen or carbon dioxide, or substantially exclude oxygen gas. For example, maintaining a non-turbulent flow of gas may include maintaining a non-turbulent flow of a gas configured for promoting healing. For example, maintaining a non-turbulent flow of gas may include humidified gas. For example, maintaining a non-turbulent flow of gas may include gas including aerosolized medicaments. For example, maintaining a non-turbulent flow of gas may include maintaining a non-turbulent flow of a gas configured for retarding the viability of pathogens. For example, the gas may include a substantial proportion of nitrogen or carbon dioxide, or substantially exclude oxygen gas. For example, maintaining a non-turbulent flow of gas may include gas including aerosolized antimicrobial agents. For example, maintaining a non-turbulent flow of gas may include gas including aerosolized antibacterial agents. For example, maintaining a non-turbulent flow of gas may include maintaining a non-turbulent flow of a gas at a temperature below the ambient temperature of the apparatus.

Methods include outletting gas from the apparatus through one or more gas outlets while maintaining positive pressure within the isolation field. For example, outletting gas from the apparatus through one or more gas outlets while maintaining positive pressure within the isolation field includes outletting gas through a particulate filter. For example, outletting gas from the apparatus through one or more gas outlets while maintaining positive pressure within the isolation field includes outletting gas through a HEPA filter. For example, outletting gas from the apparatus through one or more gas outlets while maintaining positive pressure within the isolation field includes outletting gas through a ULGA filter. For example, outletting gas from the apparatus through one or more gas outlets while maintaining positive pressure within the isolation field includes outletting gas through a HEGA filter.

Methods include providing at least one sealable access site in the apparatus sufficient for insertion of at least one human finger. For example, the apparatus may be configured of a size and shape so that an average adult human finger may be inserted through a sealable access site to obtain access to the medical site. For example, the apparatus may be configured of a size and shape so that an average adult human finger may be inserted through a sealable access site to manipulate the surface of the medical site. For example, the apparatus may be configured of a size and shape so that an average adult human finger may be inserted through a sealable access site to remove debris from the surface of the medical site. For example, the apparatus may be configured of a size and shape so that an average adult human finger may be inserted through a sealable access site to administer medicament to the medical site.

Methods include providing at least one sealable access site in the apparatus sufficient for insertion of at least one medical instrument. For example, the apparatus may be configured of a size and shape so that a specific medical instrument, or a range of medical instruments, may be inserted through a sealable access site to obtain access to the medical site. For example, the apparatus may be configured of a size and shape so that a specific medical instrument, or a range of medical instruments, may be inserted through a plurality of sealable access sites to obtain access to the medical site. For example, the apparatus may be configured of a size and shape so that a pair of forceps, a scalpel, a scissors, a suture needle, a syringe, a suction device or a monitor may be inserted through a sealable access site to obtain access to the surface of the medical site. For example, the apparatus may be configured of a size and shape so that forceps may be inserted through a sealable access site and the forceps manipulated to remove debris from the surface of the medical site. For example, the apparatus may be configured of a size and shape so that a syringe may be inserted through a sealable access site and manipulated to administer medicament to the medical site. For example, the apparatus may be configured of a size and shape so that a scalpel may be inserted through a sealable access site and the scalpel manipulated to remove damaged tissue from the surface of the medical site. For example, the apparatus may be configured of a size and shape so that multiple instruments or fingers may be inserted though multiple sealable access sites. For example, the apparatus may be configured of a size and shape so that a forceps may be inserted through a sealable access site on one side and a forceps through a separate sealable access site on the opposite side of the apparatus, so as to orient the forceps to be available to work in tandem within the interior of the apparatus. For example, the apparatus may be configured of a size and shape so that a scalpel may be inserted through one sealable access site and a suction apparatus may be inserted through a separate access site. For example, the apparatus may be configured of a size and shape so that a laproscope may be inserted through one sealable access site and an insufflator may be inserted through a separate access site. For example, the apparatus may be configured of a size and shape so that a monitor may be inserted through a sealable access site and manipulated to obtain information regarding the medical site.

Methods include providing at least one removable cover mated to a sealable access site in the apparatus. For example, a cover may be adhered to the surface of the sealable access site and then removed to provide access. For example, a cover may be fabricated from paper or plastic and be disposable. For example, a cover may be fabricated from a durable material and configured to be reusable. For example, a cover may include threading configured to reversibly mate with threading on the surface of the apparatus. For example, a cover may be configured to reversibly snap on to the surface of the apparatus. A cover may be configured to remain partially attached to the surface of the apparatus during access to the interior of the apparatus through the sealable access site. For example, a cover may be partially attached to the surface of the apparatus by a tether or an edge of the cover.

Methods include increasing the flow rate of the non-turbulent flow of gas. For example, the flow rate of the non-turbulent flow of gas may be increased to maintain positive pressure within the apparatus when a medical instrument is inserted through a sealable access site. For example, the flow rate of the non-turbulent flow of gas may be increased to maintain positive pressure within the apparatus when a human finger is inserted through a sealable access site. For example, the flow rate of the non-turbulent flow of gas may be increased at the discretion of a user of the apparatus.

Methods include decreasing the flow rate of the non-turbulent flow of gas. For example, the flow rate of the non-turbulent flow of gas may be decreased to maintain sufficient positive pressure within the apparatus when a medical instrument is removed through a sealable access site. For example, the flow rate of the non-turbulent flow of gas may be decreased to maintain positive pressure within the apparatus when a human finger is removed through a sealable access site. For example, the flow rate of the non-turbulent flow of gas may be decreased at the discretion of a user of the apparatus.

Methods include decreasing the positive pressure within the isolation field. Methods include decreasing the positive pressure within the apparatus. For example, the positive pressure may be decreased to maintain sufficient positive pressure within the apparatus when a medical instrument is removed through a sealable access site. For example, the positive pressure may be decreased to minimize gas leakage through one or more tears or openings in the apparatus. For example, the positive pressure may be decreased to minimize gas leakage from the coupling between the apparatus and the individual body. For example, the positive pressure may be decreased at the discretion of a user of the apparatus.

Methods include increasing the positive pressure within the isolation field. Methods include increasing the positive pressure within the apparatus. For example, the positive pressure may be increased to maintain positive pressure within the apparatus when a medical instrument is inserted through a sealable access site. For example, the positive pressure may be increased to maintain positive pressure within the apparatus when a human finger is inserted through a sealable access site. For example, the positive pressure within the apparatus may be increased at the discretion of a user of the apparatus.

Methods include stabilizing the position of the apparatus relative to the medical site with a restraining unit. For example, the apparatus may be stabilized in position on a surface of a region of individual body with a band or strap. For example, the apparatus may be stabilized in position on a surface of a region of an individual body through use of adhesives. For example, the apparatus may be stabilized in position on a surface of a region of an individual body through use of suction. For example, the apparatus may be stabilized in position on a surface of a region of an individual body through use of surface microstructure.

One considered method employs the apparatus in surgeries, including laparoscopic, microscopic, emergency, or combat surgery, in situations including but not limited to a hospital setting, a physician's office, a clinic, a combat arena, an emergency situation. Minor surgeries such as suturing or biopsy may also employ the apparatus. Another implementation of a method employs the apparatus to isolate a lesion, such as but not limited to, a wound, rash, pustule, or ulcer to protect the tissue from trauma or infection, to aid in healing, or to isolate a potential infectious agent within the lesion for example to avoid spreading the agent to another site or to another patient, care provider, or nearby individual. For example, methods and apparatus described herein may be of use in isolation of radioactive elements from dispersal in situations wherein a patient undergoing radiotherapy is injured. While the embodiments described herein show a gas supply, in some applications, the apparatus can also be used in the absence of gas flow to cover a lesion, tissue, or surgical site for a period of time, as during the transport of a patient.

In some aspects, an apparatus such as those described herein may be utilized in the absence of gas flow. For example, an apparatus may be utilized to cover a medical site to provide a physical barrier to contamination with the external environment for a period of time prior to the initiation of gas flow. In some aspects, an apparatus such as those described herein may be utilized in the absence of gas flow but with continued positive pressure within the interior of the structure. For example, an apparatus may be utilized to cover a medical site to provide a physical barrier to contamination with the external environment for a period of time after the discontinuation of gas flow.

With respect to the use of substantially any plural and/or singular terms herein, one can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. The terms (e.g. "configured to") can generally encompass active-state components and/or inactive-state components and/or standby-state components, unless context requires otherwise.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and the preferred vehicle will vary with the context in which the processes and/or systems and/or other technologies are implemented. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Optical aspects of implementations will typically employ optically-oriented hardware, software, and or firmware.

In a general sense, the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include, but are not limited to, a variety of consumer electronics systems, medical devices, as well as other systems such as motorized transport systems, factory automation systems, security systems, and/or communication/computing systems. The term "electro-mechanical," as used herein, is not necessarily limited to a system that has both electrical and mechanical actuation except as context may dictate otherwise.

In a general sense, the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

It will be recognized that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended to also include combinations thereof (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended to include single instances thereof (e.g., "a system having at least one of A, B, or C" would include but not be limited to systems that have A alone, B alone, C alone, A and B together, A and C together, B and C together, and/or A, B, and C together, etc.). It will be further understood that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the recited operations therein may generally be performed in any order to the extent not incompatible with the teachings herein. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The foregoing specific exemplary processes and/or devices and/or technologies are representative of more general processes and/or devices and/or technologies taught elsewhere herein, such as in the claims filed herewith and/or elsewhere in the present application.

While various aspects and embodiments have been disclosed herein, other aspects and embodiments will be apparent. The various aspects and embodiments disclosed herein are for purposes of illustration and are not intended to be limiting, with the true scope and spirit being indicated by the following claims.

What is claimed is:

1. An apparatus, comprising:
   a structure defining an aperture at an engagement surface, the structure configured to reversibly seal proximate to a wound surface on an individual body, and further defining an isolation field;
   at least one gas port;
   one or more gas inlets operably attached to the at least one gas port, the one or more gas inlets positioned proximate to the engagement surface and oriented to maintain a non-turbulent gas flow traversing at least a part of the wound surface on the individual body to direct particulate matter away from the wound surface;
   one or more gas outlets distally positioned on the structure from the one or more gas inlets to receive the particulate matter directed away from the wound surface by the non-turbulent gas flow, the one or more gas outlets configured to release a gas from the isolation field while maintaining positive pressure in the isolation field relative to an outside environment of the structure; and
   at least one sealable access site.

2. The apparatus of claim 1, wherein the structure includes a substantially shape-retaining material.

3. The apparatus of claim 1, wherein the structure includes a flexible material.

4. The apparatus of claim 1, wherein the engagement surface includes a film, and wherein the film includes a surface configured to be placed in contact with the surface on the individual body.

5. The apparatus of claim 4, wherein the film comprises:
   at least one adhesive.

6. The apparatus of claim 4, wherein the film comprises:
   an incise film.

7. The apparatus of claim 1, wherein the engagement surface comprises:
   at least one adhesive.

8. The apparatus of claim 1, wherein the engagement surface comprises:
   at least one suction device.

9. The apparatus of claim 1, wherein the at least one gas port includes a repeatably detachable connector.

10. The apparatus of claim 1, wherein the one or more gas inlets are operably attached to a tubular component.

11. The apparatus of claim 1, wherein the at least one gas port includes an inlet valve.

12. The apparatus of claim 1, comprising:
    an external gas source configured to be coupled to the at least one gas port.

13. The apparatus of claim 1, comprising:
    a flow meter coupled to the at least one gas port.

14. The apparatus of claim 1, wherein at least one of the one or more gas outlets includes a filter configured to substantially sterilize the gas released from the isolation field.

15. The apparatus of claim 1, wherein at least one of the one or more gas outlets includes a filter configured to remove the particulate matter from the gas as the gas flows through the filter.

16. The apparatus of claim 1, wherein one or more of the at least one sealable access site includes a seal fabricated from at least one flexible material.

17. The apparatus of claim 1, wherein one or more of the at least one sealable access site comprises:
    a mechanical iris structure.

18. The apparatus of claim 1, wherein the at least one sealable access site includes at least two sealable access sites, wherein each sealable access site is of a different size and shape.

19. The apparatus of claim 1, wherein the apparatus is of a size, weight and ruggedness for carrying on an individual person.

20. The apparatus of claim 1, comprising:
    at least one cover configured to reversibly attach to the engagement surface.

21. The apparatus of claim 1, comprising:
    at least one cover configured to reversibly attach to the at least one sealable access site.

22. The apparatus of claim 1, comprising:
    at least one device operably attached to the one or more gas inlets, the at least one device configured to introduce aerosol into the non-turbulent gas flow.

23. The apparatus of claim 1, comprising:
    at least one device operably attached to the structure, the at least one device configured to direct aerosol in the direction of the aperture at the engagement surface.

24. The apparatus of claim 1, comprising:
    at least one restraining unit configured to stabilize the position of the engagement surface relative to a region of the individual body.

25. The apparatus of claim 1, comprising:
    at least one sensor.

26. The apparatus of claim 1, comprising:
    at least one antenna.

27. The apparatus of claim 1, comprising:
at least one electronic controller.

28. The apparatus of claim 1, comprising:
a signal transmitter.

29. An apparatus, comprising:
a structure configured to define an isolation field, wherein the structure includes
an engagement surface configured to sealably couple to a surface on an individual body proximate to a wound, and further defining a region of the individual body that includes a medical site;
a plurality of gas inlets each positioned proximate to the engagement surface and oriented to maintain non-turbulent flow of a gas having a Reynolds number of 10 or less in parallel with at least a part of the surface on the individual body to direct particulate matter away from the wound;
at least one gas port, the at least one gas port configured for supplying the gas to the plurality of gas inlets;
one or more gas outlets positioned on the structure distal to the plurality of gas inlets to receive the particulate matter directed away from the wound by the non-turbulent gas flow, the one or more gas outlets configured to release the gas from the structure while maintaining positive pressure in the structure relative to an outside environment of the structure;
at least one sealable access site between the isolation field and an exterior of the structure; and
at least one gas source.

30. The apparatus of claim 29, wherein the structure includes a substantially shape-retaining material.

31. The apparatus of claim 29, wherein the structure includes a flexible material.

32. The apparatus of claim 29, comprising:
at least one gas supply duct operably connected to the at least one gas port and the plurality of gas inlets.

33. The apparatus of claim 29, wherein the engagement surface comprises:
at least one adhesive.

34. The apparatus of claim 29, wherein the engagement surface comprises:
at least one suction device.

35. The apparatus of claim 29, wherein the engagement surface includes a film.

36. The apparatus of claim 29, wherein the at least one gas port includes a repeatably detachable connector.

37. The apparatus of claim 29, wherein the at least one gas port includes an inlet valve.

38. The apparatus of claim 29, wherein the plurality of gas inlets are operably attached to a tubular component.

39. The apparatus of claim 29, comprising:
at least one cover configured to reversibly attach to the engagement surface.

40. The apparatus of claim 29, comprising:
a flow meter coupled to the at least one gas port.

41. The apparatus of claim 29, wherein each of the one or more gas outlets includes a filter configured to remove the particulate matter from the gas as the gas flows through the filter.

42. The apparatus of claim 29, wherein each of the one or more gas outlets includes a filter configured to substantially sterilize the gas released from the isolation field.

43. The apparatus of claim 29, wherein one or more of the at least one sealable access site includes a seal fabricated from at least one flexible material.

44. The apparatus of claim 29, wherein one or more of the at least one sealable access site comprises:
a mechanical iris structure.

45. The apparatus of claim 29, comprising:
at least one cover configured to reversibly attach to the at least one sealable access site.

46. The apparatus of claim 29, comprising:
at least one device operably attached to at least one of the plurality of gas inlets, the at least one device configured to introduce aerosol into the non-turbulent flow of the gas.

47. The apparatus of claim 29, comprising:
at least one device operably attached to the structure, the at least one device configured to direct aerosol in the direction of the region of the individual body.

48. The apparatus of claim 29, comprising:
at least one restraining unit configured to stabilize the position of the engagement surface relative to the region of the individual body.

49. The apparatus of claim 29, comprising:
at least one sensor.

50. The apparatus of claim 29, comprising:
at least one antenna.

51. The apparatus of claim 29, comprising:
at least one electronic controller.

52. The apparatus of claim 29, comprising:
a signal transmitter.

53. An apparatus, comprising:
a structure configured to define an isolation field, wherein the structure includes
an engagement surface configured to sealably couple to a surface on an individual body, and further defining a region of the individual body that includes a medical site;
a film within the engagement surface, wherein the film is oriented in parallel with at least a part of the surface on the individual body;
a plurality of gas inlets configured to maintain non-turbulent flow of a gas oriented in parallel with at least a part of the surface on the individual body;
at least one gas port, the at least one gas port configured for supplying the gas to the plurality of gas inlets;
one or more gas outlets positioned on the structure distal to the plurality of gas inlets, the one or more gas outlets configured to release the gas from the structure while maintaining positive pressure in the structure relative to an outside environment of the structure;
at least one sealable access site between the isolation field and the exterior of the structure; and
at least one gas source.

\* \* \* \* \*